United States Patent
Kay

(10) Patent No.: US 7,140,769 B2
(45) Date of Patent: Nov. 28, 2006

(54) RADIATION SENSITIVE RECORDING PLATE WITH ORIENTATION IDENTIFYING MARKER, METHOD OF MAKING, AND OF USING SAME

(76) Inventor: George W. Kay, 146 Billings St., Sharon, MA (US) 02067

( * ) Notice: Subject to any disclaimer, the term of this patent is extended or adjusted under 35 U.S.C. 154(b) by 0 days.

(21) Appl. No.: 10/510,967

(22) PCT Filed: Apr. 14, 2003

(86) PCT No.: PCT/US03/11267

§ 371 (c)(1),
(2), (4) Date: Oct. 12, 2004

(87) PCT Pub. No.: WO03/087932

PCT Pub. Date: Oct. 23, 2003

(65) Prior Publication Data

US 2005/0169433 A1      Aug. 4, 2005

Related U.S. Application Data

(63) Continuation-in-part of application No. 10/392,158, filed on Mar. 18, 2003.

(60) Provisional application No. 60/431,282, filed on Dec. 6, 2002, provisional application No. 60/372,323, filed on Apr. 12, 2002.

(51) Int. Cl.
*G03B 42/04* (2006.01)

(52) U.S. Cl. ............... 378/168; 378/165; 378/162; 378/38

(58) Field of Classification Search ............ 378/38, 378/165, 167, 168, 169, 170, 174, 182, 184; 250/580, 586, 587, 475.2, 482.1

See application file for complete search history.

(56) References Cited

U.S. PATENT DOCUMENTS 2,426,286 A  *  8/1947  Stadler .................. 378/165

(Continued)

OTHER PUBLICATIONS

Digora Intra-Oral Imaging Systems by Soredex, brochure, May 2001.

(Continued)

*Primary Examiner*—Courtney Thomas
(74) *Attorney, Agent, or Firm*—Lowrie, Lando & Anastasi, LLP

(57) ABSTRACT

A radiation-recording plate (104) can be constructed and arranged to form an image upon exposure from both a front side and a back side. The plate can include a marker (201) detectable in the image (205) after exposure and indicative of which of the front side and the back side the plate is exposed from. The marker may comprise a medium opaque to the radiation coating a region that does not interfere with reading the image when the plate is exposed from either side, or may be a void in the sensitive layer of the plate. The marker may have horizontal asymmetry about a vertical axis relative to a normal image orientation, or the marker may have vertical asymmetry about a horizontal axis relative to a normal image orientation. The marker may further comprise a front side marker and a back side marker whose appearance in an image on the plate indicates exposure from the front side or the back side respectively. A method of identifying a side from which a radiation-recording plate has been exposed to radiation may comprise: incorporating in the plate (104), in a position that substantially does not interfere with an image area of the plate, a marker (201) whose appearance in the image identifies which side the plate is exposed from; exposing the plate to the radiation; and observing the image (205) for the identification of the side of the plate exposed. A method of making a radiation sensitive plate having at least one radiation sensitive layer may comprise: providing a film sensitive to the radiation on a first side of the radiation sensitive plate; and applying a suspension of a heavy metal in a binder to a region of a second side of the radiation sensitive layer.

52 Claims, 12 Drawing Sheets

U.S. PATENT DOCUMENTS

| | | | | |
|---|---|---|---|---|
| 4,356,398 | A | 10/1982 | Komaki et al. | 250/582 |
| 4,578,581 | A | 3/1986 | Tanaka et al. | 250/587 |
| 4,598,207 | A | 7/1986 | Naruse et al. | 250/484.4 |
| 4,625,325 | A | 11/1986 | Beraudo | 378/168 |
| 4,803,359 | A | 2/1989 | Hosoi et al. | 250/586 |
| 4,814,616 | A | 3/1989 | Saotome | 250/586 |
| 4,829,548 | A | 5/1989 | Halm et al. | 378/38 |
| 4,835,398 | A | 5/1989 | Nakamura | 250/484.4 |
| 4,933,558 | A | 6/1990 | Carter et al. | 250/582 |
| 4,965,455 | A | 10/1990 | Schneider et al. | 250/484.4 |
| 5,123,040 | A * | 6/1992 | Fabian | 378/182 |
| 5,434,418 | A | 7/1995 | Schick | 250/370.11 |
| 5,696,805 | A | 12/1997 | Gaborski et al. | 378/54 |
| 6,042,267 | A | 3/2000 | Muraki et al. | 378/169 |
| 6,055,326 | A | 4/2000 | Chang et al. | 382/132 |
| 6,174,330 | B1 | 1/2001 | Stinson | 623/1.34 |
| 6,255,667 | B1 | 7/2001 | Rantanen | 250/585 |
| 6,303,101 | B1 | 10/2001 | Klaveness et al. | 424/9.1 |

OTHER PUBLICATIONS

D.A.Miles, DDS, MS, FRCD, Understanding Digital Radiography, posted on Internet by dentalproducts.net Originally published in Dec. 2000 Dental Practice Report, http://www.dentalproducts.net/sml/0012/miles0012/miles0012a.asp, Apr. 27, 2002.

Fujifilm Products, Fuji Computed Radiography, http://home.fujifilm.com/info/products/inform/fuji_radio.html, Apr. 27, 2002.

Agfa, Radview Phosphor Scanner, http://ndt.agfa.com/bu/ndt/indes.nsf/EN/computedradiography.htm, Apr. 27, 2002.

A/T ScanX™ Digital Imaging System PN73400, Operator's Manual, 2002.

X-Ray Mass Attenuation Coefficients—BISMUTH, 3 pp., http://physics.nist.gov/PhysRefData/XrayMassCoef/ElemTab/z83.html, Dec. 14, 2002.

Digora Fmx—Soredex, Technical data, http://www.soredex.com/digora_fmx_data.shtml, Nov. 21, 2002.

Terry, B.R., DMD et al., Digital Radiography, http://www.rootcanalspecialist.com/digitalradiography.htm, Apr. 27, 2002.

Digora Fmx—Soredex, Technical data, Aug. 2002.

Digora Intra-Oral Imaging Systems by Soredex, http://webspace.dialnet.com/preseli.computers_pcs/Digora.htm, Nov. 21, 2002.

* cited by examiner

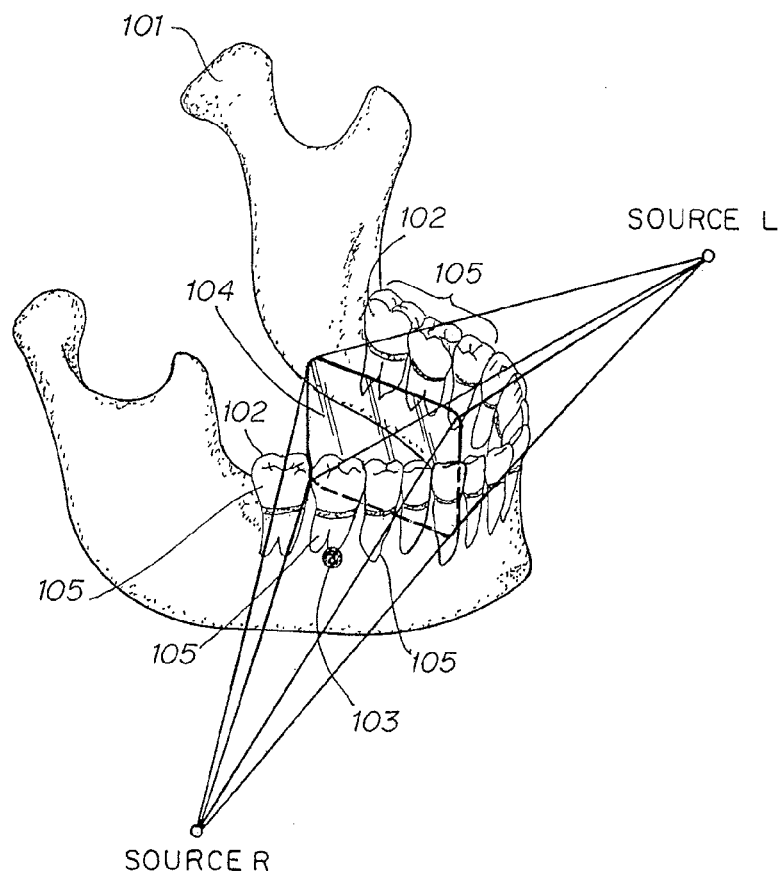
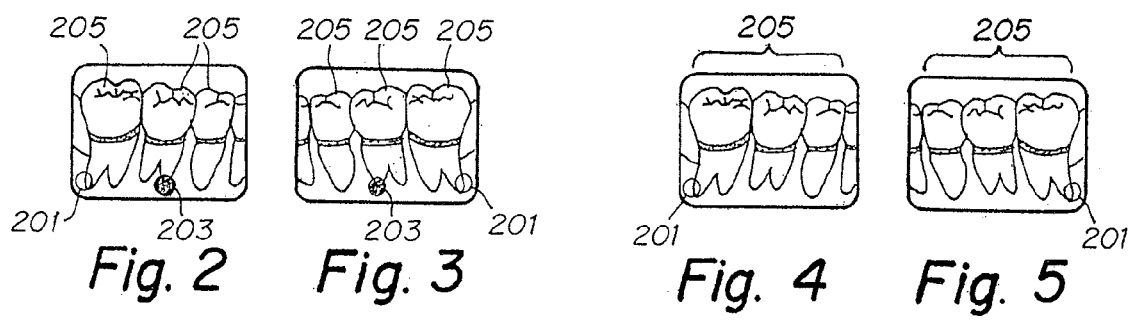
Fig. 1
Fig. 2  Fig. 3  Fig. 4  Fig. 5

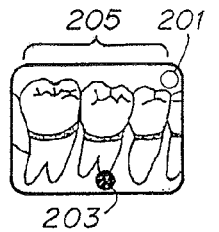
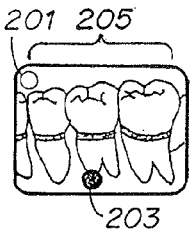
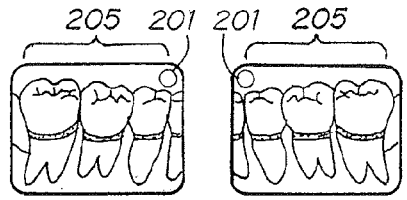
Fig. 6   Fig. 7   Fig. 8   Fig. 9
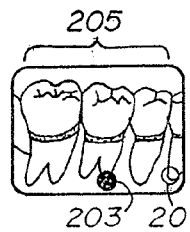
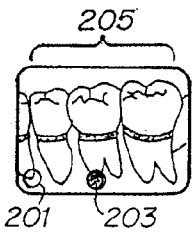
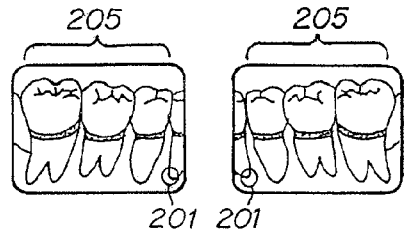
Fig. 10   Fig. 11   Fig. 12   Fig. 13
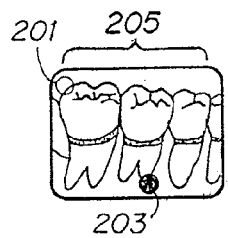
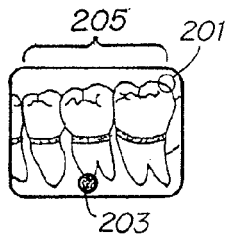
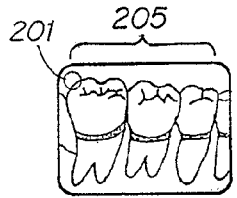
Fig. 14   Fig. 15   Fig. 16   Fig. 17
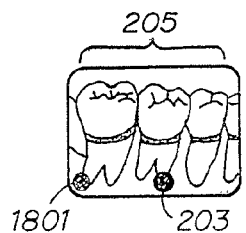
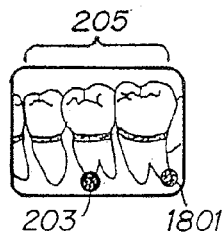
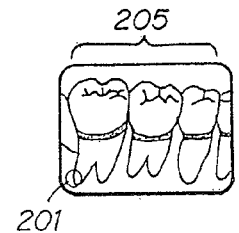
Fig. 18   Fig. 19   Fig. 21   Fig. 22

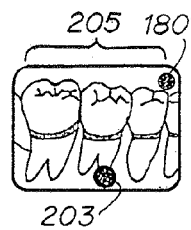 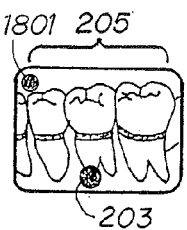 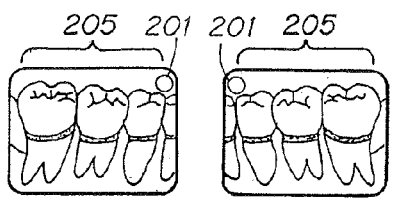
Fig. 22    Fig. 23    Fig. 24    Fig. 25
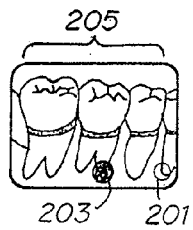 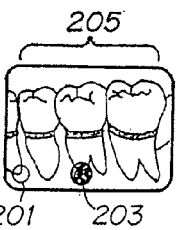 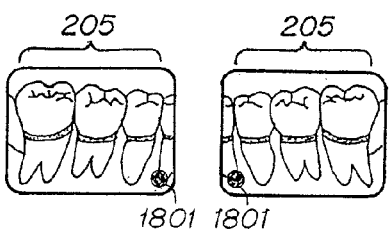
Fig. 26    Fig. 27    Fig. 28    Fig. 29
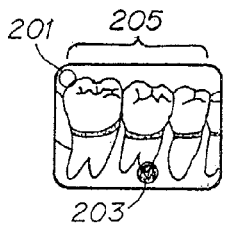 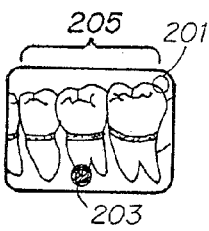 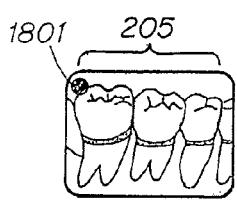 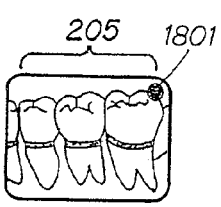
Fig. 30    Fig. 31    Fig. 32    Fig. 33

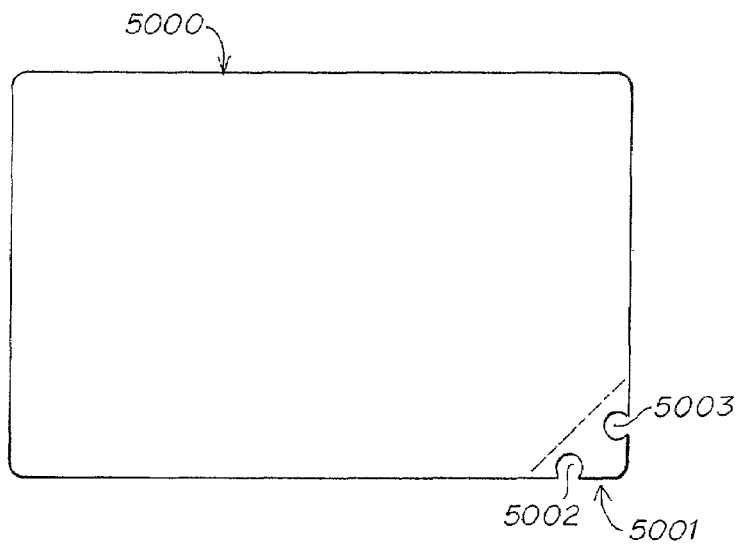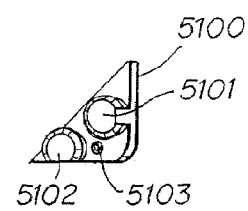
Fig. 50     Fig. 51
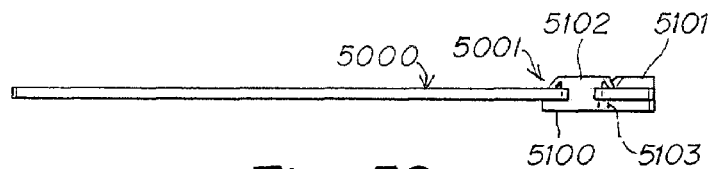
Fig. 52
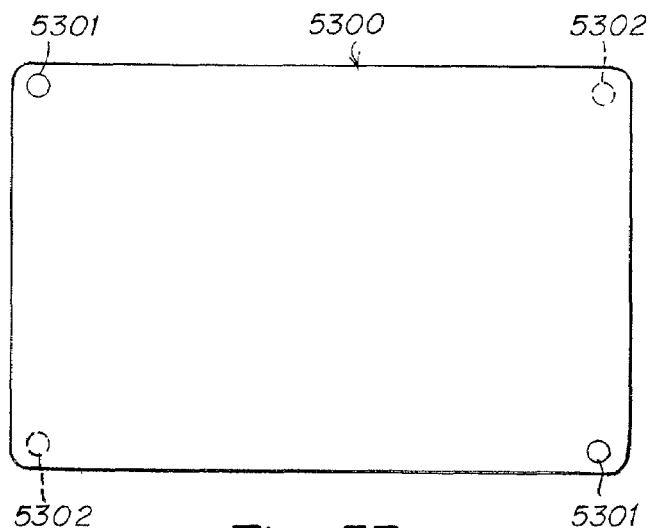
Fig. 53

US 7,140,769 B2

RADIATION SENSITIVE RECORDING PLATE WITH ORIENTATION IDENTIFYING MARKER, METHOD OF MAKING, AND OF USING SAME

CROSS REFERENCE TO RELATED APPLICATION

This application claims priority under 35 U.S.C. § 119(e) to U.S. Provisional Application Ser. No. 60/372,323, entitled "METHOD FOR INTERNALLY LABELING THE ORIENTATION OF EXPOSURE OF RADIATION-SENSITIVE PLATES BY PRODUCING A RECOGNIZABLE PATTERN WITHIN THE INFORMATION SET PRODUCED BY SUCH EXPOSURE," filed on Apr. 12, 2002, and to U.S. Provisional Patent Application Ser. No. 60/431,282, entitled "A RADIATION SENSITIVE RECORDING PLATE, A METHOD OF MAKING SAME AND A METHOD OF RECORDING AND ORIENTING IMAGES," filed on Dec. 6, 2002, and to U.S. patent application Ser. No. 10/392,158, entitled "A RADIATION SENSITIVE RECORDING PLATE AND METHOD OF MAKING AND USING SAME," filed on Mar. 18, 2003, all of which are herein incorporated by reference in their entirety.

BACKGROUND

This application relates generally to image processing. More specifically, the application relates to identifying image orientation. Yet more specifically, the application relates to identifying image orientation in medical and dental X-ray shadow-grams.

Images produced in conventional roll-film cameras, on film, are easy to orient correctly because the camera is constructed in such a way that the emulsion of the film always faces the lens. Because of the shapes of film cassettes and cameras, the film cannot be inserted in modern cameras with the emulsion facing away from the lens, so it is always known that the light, or other radiation recorded by the film, struck the film from the emulsion side. Thus, when orienting slides for projection, or film images for viewing on a light box, it is always known to put the emulsion toward the projection lens in the slide projector, or to put the film on the light box with the emulsion towards the viewer. When that is done, the image seen by the viewer, whether projected or viewed on the light box, will have a known defined correspondence with the orientation of the objects in the original scene. Moreover, even if orientation is lost, reorienting based on determining where the emulsion is will reestablish proper orientation.

Likewise, digital images produced using cameras with detectors such as charge-coupled devices (CCDs) that are sensitive to exposure from one side only are inherently unambiguous. The cameras used to produce such images are physically constructed and arranged with a lens or lens mount in a fixed position relative to the detector, so that the direction from which the exposing radiation strikes the detector is always known. CCD sensors used in dental digital radiography also are physically constructed and arranged to produce a diagnostic image only when exposed from the proper direction. Such CCD sensors include a radiopaque element on the side away from the intended direction of exposure.

The problem is somewhat more complicated for dental or medical diagnostic images produced on conventional film. One common type of dental or medical diagnostic image is a shadow-gram produced by placing a radiographic film on one side of the object to be imaged and a source of radiation to which the film is sensitive on a diametrically opposite side of the object to be imaged. The radiation, for example X-radiation, casts a shadow of the object to be imaged on the film, thus revealing density variations within the object whose shadow has been cast. When a standard orientation of the examined object is used, and the film is viewed from the same side as the radiation source exposing the emulsion, the laterality, i.e. right versus left, of the object is preserved, because the viewer can unambiguously discern right from left side by observing the image alone. However, medical or dental X-ray film can be exposed and viewed from either side because the film is transparent to both X-rays and visible light. To further complicate matters of orientation, an emulsion is often applied to both sides of the film in order to lower the dosage of radiation required to produce the diagnostic image, by increasing the sensitivity of the film. However, film thus constructed cannot be oriented on the basis of which side has an emulsion. Thus, it is desirable to identify from which side the film was exposed to radiation and so indicate the side from which it should be viewed.

Conventionally, and due in part to its high sensitivity to visible light, as well as to X-rays, radiographic film is usually held in an opaque cassette which not only prevents exposure to visible light, but also limits X-ray exposure to one side of the film, only. The side of the cassette through which large format film, such as that used for medical X-ray applications, is exposed often includes radiopaque labels indicating various patient information, including patient name, date of exposure, side of the patient (e.g., left or right arm), etc., for example, which provide a clear indication embedded in the image of the side of the film from which the exposure was made. If such labels are used, reversal of the image by viewing from the side opposite the side of exposing incident rays also causes the label characters to reverse, clearly indicating the reversed orientation of the diagnostic image. Systems also exist (e.g., Planmeca's pantomograph) which incorporate within the film cassette a mechanism which automatically optically imprints on the margin of the film, and therefore the image, pertinent patient, exposure, and orientation data during the exposure of the film. Often physical features, e.g., notches in the edge or corner of the film or keyways that orient the cassette itself to a cassette holder within the apparatus exposing the object, are used to further ensure that a consistent orientation of the film in the cassette and the exposure apparatus, and thus, the relative orientation of film and the image recorded on it to the object, is obtained and retrievable independently of the structure represented in the diagnostic image itself. The "back side" of the cassette is itself at least partially radiopaque over its entire surface, so as to prevent accidental exposure from the wrong side. The spatial orientation of the original form creating the shadow in the image is thus clearly and unambiguously defined. However, this clear and unambiguous outcome relies either upon the mechanical features noted above, or upon the X-ray technician properly loading the cassette and placing the orienting labels, followed by exposing from the correct side. Otherwise, if the positioning of the film or the cassette is improper, the image produced visually reflects the improper orientation and the process and must be repeated.

Unlike the large format films described above, dental intraoral films are conventionally provided prepackaged in packets, which may be disposable and which are often flexible. Because intraoral films must be small enough to be positioned within the mouth, there is little room available for the types of labels described above. In the case of conventional dental intraoral films, proper orientation is identified by a raised or embossed bump on the film and packet that points away from a radiopaque backing in the packet that prevents or limits inadvertent exposure from the wrong side. The bump, which projects from the plane of the film in the direction from which the shadow is cast, is a permanent feature of the film and persists as marker of the orientation in the dimension perpendicular to the plane of the film, providing a method by which the viewer can identify the side of exposure. If an exposure is made from the wrong side, the resulting image is recognizably undiagnostic because of its degradation caused by the radiopaque backing contained within the packet. The radiopaque backing, typically a textured heavy metal foil, causes exposure from the wrong side to appear in the image as a textured pattern, while the embossed feature preserves and identifies the orientation information for the viewer. As with medical X-rays in which a proper outcome is assured by correct loading of the cassette, a proper outcome using intraoral dental films is assured only by correct assembly of the packet at the factory, followed by correct handling by the dental X-ray technician. The degradation of the image evidencing improper exposure orientation of the film, which results in the reversal of the diagnostic image when the bump feature is used to orient the image, is, however, immediately obvious to the viewer, assuring that mistaken identification of features in the image is highly unlikely and traceable. This combination of an orientation feature and a feature preventing exposure from the wrong side is now conventional.

By convention, dental intraoral films are produced in a variety of generally rectangular standard sizes, with rounded corners. Also by convention, when prepared for viewing, they are grouped in an anatomical arrangement in a holder called a mount. Standard mounts hold films in one of two orientations only: with the longer dimension of the film in a horizontal orientation, henceforth in this application referred to as "landscape" orientation; and with the longer dimension of the film oriented vertically, henceforth referred to in this application as "portrait" orientation.

In keeping with conventions of viewing of radiographic images, on film or on a computer monitor, and for nonambiguity and clarity of the descriptions, the frame of reference for principal directions is based on the image plane, itself. Up shall be a direction generally from any point in the image toward a top of the edge of the image, while down is in an opposite direction. With the up direction oriented in a natural fashion for a viewer, left and right correspond to the viewer's left and right. Vertical corresponds to the direction of a line running up and down from any point in the image.

U.S. Pat. No. 4,625,325 describes a method which incorporates both conventional radiographic film and phosphor in the same process with radiopaque material. The device described patented therein includes a film packet, similar to the intraoral dental film packet described above. The device also incorporates a pocket for holding a plate which is inserted by the technician prior to the exposure of the film. The plate, which is coated with a phosphor on the side facing the film and radiation source and which incorporates radiopaque material on the opposite side, is positioned adjacent to the film in the packet. The plate is an image amplifier. During the exposure, the film is exposed both by X-rays impinging directly on the film and by the phosphorescence emitted by the plate phosphor stimulated by the same X-rays. Those X-rays which have passed both the film and the phosphor are absorbed by the radiopaque backing, thereby limiting tissue exposure downstream of the recording surfaces. The packet, film and plate are held by a jig in a position such that the film and plate can only be exposed from one side. The phosphor only functions as an amplifier to provide improved signal-to-noise ratio and to lower the radiation dose per exposure. The phosphor film does not function as a storage phosphor holding a latent image, and is not scanned to produce a diagnostic digital image. Furthermore, no issues of image orientation ambiguity from a digital electronic image result from the process, because the image is recorded on conventional radiographic film, as before.

Radiosensitive storage phosphor plates have recently started displacing conventional radiographic emulsion film for recording medical and dental images. Advantages including superior sensitivity, lack of dependence on toxic chemical processing fluids, relative insensitivity to ambient light, reusability, and the ease of digital data storage and transmission all stimulate the growth of this technology. The image orientation issues noted above with respect to conventional film; however, as well as new image orientation problems, for example resulting from the use of image processing software, manifest themselves in the use of such radiosensitive plates. As discussed above, the orientation of the image produced by film technology was identified unambiguously by the presence of a three-dimensional object, namely the bump protruding from the film surface toward the object casting the shadow, providing a permanent and absolute reference in a dimension perpendicular to the plane of the film. The other two dimensions, superior-inferior and anterior-posterior are inferred from the anatomical structures in the image. Unlike the image incorporated into a three-dimensional physical object, i.e., the film with a bump, the images produced by existing phosphor plate technologies are stored and displayed as two-dimensional views without a complete, definite, and permanent indicator of the direction of exposure or of viewing. Incomplete references or markers, as discussed below are incorporated into the existing systems; however, none of the systems are unambiguous, permanent, or complete by virtue of their design.

Although radiosensitive plates are sensitive to a specific, diagnostic radiation type, e.g., X-rays, they are substantially insensitive to visible light for the purposes of registering an image. They can be handled in ordinary room light, absent the usual cassette until the time of the exposure. They are, for sanitary and other purposes such as reducing wear and tear on the phosphor, inserted into radiolucent plastic film sleeves before each use. The plates are also reusable to produce multiple images over a period of time. Erasure, by prolonged exposure to intense visible light, and repackaging in the disposable radiolucent plastic film sleeves is done by a technician at the point of use, rather than at the point of manufacture.

A scanner, through laser illumination, stimulates the phosphor to emit light in an amount which depends on the amount of prior exposure to X-rays, and which in turn is registered as data signal. Currently, commercially available phosphor-based digital radiology systems use plates having a polymer sheet substrate supporting a pastel-colored phosphor layer applied to one surface of the substrate. The other surface of the substrate appears black. For the purpose of this application, the side of the plate which is intended by the manufacturer as the preferred side to be read, e.g., by the scanner, to produce the diagnostic image shall be referred to as the "front side", while the opposite side of the plate and sensitive layer shall be referred to as the "back side" henceforth. For practical reasons related to the current technology, the side of the plate that is generally intended as the side to be scanned ("front side") is also the side on which the sensitive layer is nearer the surface of the plate and is visible, thereby available for excitation by the scanning mechanism.

Even though the sensitive layer, e.g., phosphor, is available for scanning from one side, the "front side", only, it can be exposed and register a latent image from either side, and in some commercial systems equally well. As a result of the possibility that the shadow recorded by the sensitive layer, e.g., phosphor, could have been cast from either side of the plane of the plate, the recorded latent image as well as the visible image resulting from its scan are ambiguous with respect to their laterality. Thus, when recording bilaterally symmetric structures, e.g., left or right jaw, mirror images result, which can be easily confused since they are not uniquely oriented. Therefore, the two sides of the body (or mouth) can be confused by the viewer of the image, resulting in erroneous diagnosis and/or treatment. As a result, current commercially available phosphor plate systems, such as those produced by Air Techniques Inc. and Gendex™, provide detailed explicit instructions to package and expose plates in a specific orientation, so as to preserve image orientation.

Some digital systems employ techniques analogous with technology used in conventional emulsion film. For example, Digora™ (available from Soredex) system phosphor plates incorporate a slightly radiopaque layer on the "back side" of the plate, which reduces patient irradiation by rays that pass through the plate and into the patient. The radiopacity of the backing is featureless, but the backing degrades an image exposed by irradiation from the "back side."

Systems such as Scan-X™ (available from Air Techniques Inc.) and Denoptics™ (available from Gendex Dentsply) each feature a distinctive marker. The markers are distinctively shaped, either a lower case letter "a" opaquely printed over the "front side" of the phosphor or a small open circle evident as an absence of the phosphor in a localized area, respectively. These markers are incorporated at the time of fabrication of the plates by the manufacturer and are constructed in such a way as to always be read from the phosphor by the scanner in a constant fashion independent of any exposure variables. The result of the presence of a marker produced by either of the above variants, i.e. Scan-X and Denoptics, in fabrication is a diminution, or absence, of phosphorescence from the area of the plate so altered, during scanning. This relative lack of signal is reflected in the visible scan image as a distinct shape corresponding to the shape and the location of the marker on the phosphor plate.

Any features of such a marker that are either asymmetric or placed asymmetrically with respect to a vertical axis of symmetry of the plate, or both, become represented by similarly asymmetric features in the image of the plate following a scan. Furthermore, this marker image becomes reversed with respect to its laterality either in respect to its asymmetric location or its internal asymmetry as a result of software horizontal reflection of the scanned image. As the placement of the source of the radiation during the exposure has no influence over the appearance of the image of such marker, this marker is well suited as an indicator of any reversal of laterality of the entire image following the completion of the scan.

For practical reasons, namely because the image produced by each of the commercially available phosphor plate technology systems can be displayed and viewed in one of four orientations only, which orientations correspond to the conventional orientations for emulsion-based radiographic film mounts, and which orientations are separated by steps of ninety degree rotation relative one another, the rotational transformations of the image (and the plate position) in this application will also be confined to ninety degree steps, or multiples thereof. Thus the available set of orientations to consider for any image will be the two "landscape" and two "portrait" possibilities, i.e., one right side up and one up side down for each category.

The configuration shown in FIG. 1 illustrates generally how a dental X-ray plate can be used to produce images, X-ray shadowgrams, of a patient's lower jaw and teeth. The particular physiological structure is illustrative of the symmetry problem discussed above. However, the problem occurs in connection with many physiological structures as a result of the inherent symmetry present in most biological systems, particularly humans and animals. The configuration of FIG. 1 is now described as it relates to conventional digital dental X-ray plates. Later, in the DETAILED DESCRIPTION, the configuration of FIG. 1 is referenced as it relates to aspects of the invention, which may be practiced in this configuration, as well as other suitable configurations.

The anatomical structure illustrated in FIG. 1 is a human lower jaw, i.e., a human mandible 101, having a set of teeth 102 set therein. Although not shown, for clarity, it may be assumed that the mandible 101 and teeth 102 are part of a living patient's body, covered with the soft tissues, etc. This particular patient has a diagnostically significant condition, e.g., an abscess, denoted by filled circle 103. A dental technician, dentist or other has placed a conventional digital dental X-ray plate 104 in the patient's mouth in a position suitable for capturing a shadowgram of three of the patient's posterior teeth 105 on either side of the patient's mouth. Although in actual practice, the plate 104 would be placed close to the teeth whose shadowgram is being recorded, so as to produce a clear image, for the convenience of illustration the plate 104 is shown centered between the teeth of the left side and the teeth of the right side of the patient's mouth. Finally, two alternative locations for X-ray sources, SOURCE L and SOURCE R, are shown. X-ray source, SOURCE R, produces the images shown in FIGS. 2 and 3, while X-ray source, SOURCE L, produces the images shown in FIGS. 4 and 5. FIGS. 2, 3, 4 and 5 are now described, with reference back to FIG. 1, as required.

FIGS. 2, 3, 4 and 5 illustrate four images that can be produced using a conventional digital X-ray plate exposed from each of two sides, using each of two differently located sources, e.g., positioned at SOURCE L and SOURCE R. Because the reference conventional commercial plate has an open circle mark on the "front side" of the plate, in one corner, an open circle 201 appears in each of the images. Images produced by source, SOURCE L, include images 205 of posterior teeth 105 and images produced by source, SOURCE R, include both images 205 of posterior teeth 105 and an image 203 of diagnostically significant condition 103. In conventional digital X-ray plate usage, the open circle is present on the "front side" of the plate and is intended to direct the technician, dentist or other to face that side of the plate toward the exposure source. However, such a consistent usage is not guaranteed.

If the plate were to be consistently exposed from only one side (e.g., "front side"), then this marker would provide an absolute reference of laterality by eliminating confusion introduced by horizontally flipping of the image. Such reflection results in the displacement of the open circle marker from the lower right or the upper left corners of the image to the lower left or the upper right in the images which are in "landscape" orientation. The displacement would be the reverse for "portrait" orientation. Although recommended, and consistent with best practice, such a consistent exposure of the plate from the sensitive side is not guaranteed either in the loading of the plate into the sleeve or in its placement during exposure itself.

It should be noted that certain predictable rules of translocation govern a system composed of a radiographic plate, the image it holds, the long and the short axes of symmetry of the plate or its image, and a universe of combinations of two motions, a reflection through a vertical plane perpendicular to that of the image and a 90 degree rotation around an axis perpendicular to the plane of the plate at the intersection of its long and short axes of symmetry.

The reflection of the image within this system can occur through one of two modes. The first mode involves casting the shadow, i.e., registering the image, onto the sensitive layer, e.g., phosphor, from one side of the plate, e.g., "back side", and reading it off the opposite aspect of the sensitive layer, e.g., "front side". Only one instance of this mode may occur per image. This mode of reflection shall henceforth be referred to as "pre-exposure" reflection in this application. The second mode involves the use of an image processing software tool which reflects right-for-left any selected image. The number of instances of this mode of reflection is not theoretically limited. This mode of reflection shall henceforth be referred to as "software" reflection in this application.

Rotation has two distinct modes. The first mode is a physical rotation of the plate, together with its markers, relative to the object to be imaged prior to exposure involved in changing the orientation from "landscape" to "portrait", and if continued, back to "landscape". This mode of rotation shall be referred to henceforth in this application as the "pre-exposure" mode of rotation. The second mode of rotation can occur several ways. After exposure, the plates, being small, unattached objects are free to be moved and become randomized in orientation. These plates are later removed from their sleeves and arbitrarily rotated as to fit into a plate holder mechanism of the scanner, the constraint at this stage being that the "front side" must face the sensor. Once the images are produced on the computer screen, the operator uses the image processor to align the images in proper superior-inferior orientation by rotating them. This software-mediated rotation is limited to multiples of ninety degrees and is the mechanism through which correct "landscape" and "portrait" orientation as well as superior-inferior relationship is achieved as needed. All three of the rotations given above maintain the relationship between the location of the marker and the details of the shadow-gram. They also preserve laterality. The several mechanisms of rotation comprising the second mode of rotation occur after the sensitive layer is exposed and will henceforth in this application be referred to as "post-exposure" mode of rotation. When a "post-exposure" rotation results in a 180 degree rotation, the resulting transformation is equivalent to a reflection of the entire recorded image through a point located at the intersection of the long and the short axes of symmetry of the plate.

In order to better understand the discussion below in the DETAILED DESCRIPTION of how the structures according to aspects of the invention unambiguously identify correct and incorrect image orientation, first a discussion of possible transpositions of the image is given.

Within the context of this application, the two modes of reflection and two modes of rotation comprise the universe of orientation transformations allowed by the laws of physics and by the graphic functions included in the software of the image processors typically provided with digital radiography systems. For the purposes of this example, and in order to demonstrate the inability of only a conventional marker to differentiate various transformations, a marker 3811, as defined earlier, shall be placed in the lower right corner, as viewed from the "front side", of a plate in a "landscape" orientation. In FIG. 38 the images 3801, 3802, 3803, 3804, 3805, 3806, 3807 and 3808 within the same row (e.g., 3801, 3802, 3803 and 3804; or 3805, 3806, 3807 and 3808) are related to their neighboring images by one ninety-degree "post-exposure" rotation for each step. On the other hand images within the same column (e.g., 3801 and 3805, etc.) are related by a "software" reflection through a vertical plane perpendicular to that of the plate. As the images 3801, 3802, 3803 and 3804 and also the images 3805, 3806, 3807 and 3808 illustrate, rotation alone allows only two marker 3811 locations each for both the "portrait" and the "landscape" orientations of the image. That is to say that if the image is only rotated (i.e. they lie within the same row in FIG. 38), there are two allowed locations of the marker 3811 for the "landscape" orientation 3801 and 3803 or, the lower right and the upper left corner, and two allowed locations for the marker in the "portrait" orientation 3802 and 3804: lower left and upper right corner of the image. It is also evident from FIG. 38 that for both the "portrait" and for the "landscape" orientation a combination of rotation within the plane and reflection through a perpendicular plane manipulation, as described earlier, is sufficient to generate all the possible locations of the marker. It is also evident that all paths involving an odd number of reflections (i.e. one which generates a net shift of the image to a different row in FIG. 38) are qualitatively different from the paths involving an even number of reflections (i.e. no net shift of row generated in the process). Therefore, assuming an original position of the marker 3811 in the lower right corner in a "landscape" orientation as in image 3801, it is clear that relative to original image 3801, the laterality of image 3803 has not been reversed but that of image 3809 has been. Furthermore, without the knowledge of the original image 3809, 3810 it is possible to deduce its laterality by observation of the marker location and the "portrait" vs. "landscape" orientation of the plate. It should also be noted that teeth of the lower and the upper jaw are significantly enough different to allow their recognition in radiographic images thereby preserving orientation in the superior-inferior dimension. By analogy, if the long arrow 3810 is assumed to serve as a recognizable index for the superior direction, and the short arrow 3809, the forward direction, then only images 3801 and 3805 represent images properly oriented with respect to the superior-inferior dimension. Furthermore, of those two, only image 3801 has preserved the original laterality of the object casting the shadow. Further complicating the situation is that the plate could have been exposed from the "back side" and viewed from the "front side", resulting in image 3805. This image must be reflected horizontally to be viewed in the "correct" orientation of image 3801.

Suppose, for the purpose of analyzing the images in FIGS. 2, 3, 4 and 5, that the technician, dentist or other exposing this patient's digital dental X-ray plate 104 has oriented the "front side" defined above, carrying the open circle, and consequently the sensitive side of the plate 104, toward the X-ray source located at the position SOURCE L, and in the lower right corner of the plate 104 as viewed from the direction of the X-ray source located at the position SOURCE L. FIG. 3 is the image read from the "front side" of the plate 104, when the plate so oriented is exposed by an X-ray source at the location designated SOURCE R. If the dentist reading such an image is aware that the exposure has been made from the "wrong" side, i.e., the "back side", of the plate, the dentist can use image processing software to reorient the image by horizontally flipping the image, as shown in FIG. 2. Mark 201 is transposed from the right to the left, side of the image. The same plate 104, oriented the same way, but exposed from an X-ray source at the location designated SOURCE L, when read from the sensitive side of the plate 104, produces the image shown in FIG. 5. The image of FIG. 4 can be inadvertently produced by manipulation of the image processing software to horizontally flip the image of FIG. 4. Since FIGS. 2 and 4, and FIGS. 3 and 5, are respectively indistinguishable without knowing from which side the plate 104 was exposed, there is no way to determine which side of the patient's jaw the condition 103, seen only in the images in FIGS. 2 and 3, is on. If condition 103 does not produce any externally observable symptoms, the X-ray image may be the only evidence upon which the dentist can rely for determining the location to treat. An ambiguity is introduced into the record that cannot be resolved without another exposure of the patient to radiation. Digital plate technology in its current form does not assure that the orientation of the image can be ascertained. Current technology instead relies on the statistical likelihood that the technician will expose the film correctly vast majority of the time. However, no unambiguous marker of the exposure orientation exists within the image. The following four examples illustrate the problem of a lack of an internal reference:

1. If only one image is available for viewing independently of other patient information, the viewer will not be able to identify the correct orientation of the image, except by making an assumption that it was exposed from the "front side".

2. If a technician is consistently making the error of exposing the films from the "back side", unknown to the viewer, the viewer will conclude when comparing images that images (in fact) exposed and oriented correctly are incorrectly oriented (which is not factually correct), thus compounding the problem.

3. A disgruntled or incompetent employee can wreak havoc with the records without anyone realizing it, or having a way of tracing the problem by using software to alter the apparent orientation of images in the records.

4. A person with fraudulent intent can expose the plate intentionally from the "back side" in order to make the image appear as though it depicts the opposite side of the body.

The analysis of FIGS. 6, 7, 8 and 9 is similar to FIGS. 2, 3, 4 and 5, respectively, except for the initial orientation of the plate. These images are produced by a plate 104 oriented with an open circle, and consequently the sensitive side of the plate 104 oriented toward the X-ray source located at the position SOURCE L, but in the top left corner of the plate as viewed from the direction of the X-ray source located at the position SOURCE L.

FIGS. 10, 11, 12 and 13 represent images produced by a plate 104 oriented with an open circle, and consequently the sensitive side of the plate 104 oriented toward the X-ray source located at the position SOURCE R, but in the bottom right corner of the plate as viewed from the direction of the X-ray source located at the position SOURCE R.

FIG. 10 shows the image produced by SOURCE R, in which the open circle 201 is in the lower right corner. FIG. 11 can be inadvertently produced by a horizontal flip of the image of FIG. 10 using image processing software. FIG. 12 shows the result of exposing the plate using SOURCE L. In order to view the image in an orientation expected by the dentist, the image of FIG. 12 can be horizontally flipped to produce the image of FIG. 13. Similarly to the situation described above in connection with FIGS. 2, 3, 4 and 5, FIGS. 10 and 12 are inherently indistinguishable, as are FIGS. 11 and 13.

The analysis of FIGS. 14, 15, 16 and 17 is similar to FIGS. 10, 11, 12 and 13, respectively, except for the initial orientation of the plate. These images are produced by a plate 104 oriented with the open circle, and consequently the sensitive side of the plate 104 oriented toward the X-ray source located at the position SOURCE R, but in the top left corner of the plate as viewed from the direction of the X-ray source located at the position SOURCE R.

SUMMARY OF INVENTION

A radiation-recording plate can be constructed and arranged to form an image upon exposure from both a front side and a back side. The plate can include a marker detectable in the image after exposure and indicative of which of the front side and the back side the plate is exposed from. The marker may comprise a medium opaque to the radiation coating a region that does not interfere with reading the image when the plate is exposed from either side. The plate may be sensitive to X-radiation, and the medium may comprise one of a heavy element, an alloy including a heavy element, a compound including a heavy element or a salt of a heavy element. The medium could be one of Pb, Sn, Bi, I and Ba. The medium could be a heavy metal suspended in a binder applied to the region. The marker may have asymmetry about at least one axis. The marker may have horizontal asymmetry about a vertical axis relative to a normal image orientation, or the marker may have vertical asymmetry about a horizontal axis relative to a normal image orientation. The marker may further comprise a back side marker whose appearance in an image on the plate indicates exposure from the back side.

The plate may have a layer sensitive to the radiation that is readable only from the front side, the back side marker further comprising at least one of a material that enhances reading the sensitive layer and a material that attenuates reading of the sensitive layer. Such a back side marker may further comprise at least one of a material that enhances exposure of the plate in a defined region and a material that attenuates exposure of the plate in the defined region. The back side marker may further comprise one of a heavy element, an alloy including a heavy element, a compound including a heavy element or a salt of a heavy element. The medium may be one of Pb, Sn, Bi, I and Ba.

The plate may further comprise a front side marker whose appearance in an image on the plate indicates exposure from the front side. This plate may further have a layer sensitive to the radiation that is readable at least from the front side, the front side marker further comprising at least one of a void defined in the layer sensitive to the radiation, a material that enhances a signal returned in the area of the marker when reading the sensitive layer and a material that attenuates the signal returned in the area of the marker when reading the sensitive layer. The plate may be readable only from the front side by exciting the layer sensitive to the radiation with an excitation wavelength to generate a return signal at a return signal wavelength, the front side marker functionally opaque to at least one of the excitation signal wavelength and the return signal wavelength. The front side marker may further comprise one of a heavy element, an alloy including a heavy element, a compound including a heavy element or a salt of a heavy element. The medium may be one of Pb, Sn, Bi, I and Ba. The front side marker may further comprise a void defined in the layer sensitive to the radiation.

The marker may have asymmetry about at least one axis and the marker further comprising a front side marker and a back side marker. The marker can have either horizontal asymmetry about a vertical axis or vertical asymmetry about a horizontal axis, relative to a normal image orientation. In this case, the front side marker may further comprise: a region defined to have a shape of an arrow pointed in a first direction when viewed from the front side. The back side marker may further comprise: a region defined to have a shape of an arrow pointed in a second direction different from the first direction when viewed from the front side. The back side marker can be positioned so as to obscure the front side marker when the plate is exposed from the back side and read from the front side. The plate may include another sensitive layer, wherein the back side marker is disposed between the sensitive layer and the other sensitive layer, and the plate further comprising another front side marker relative to the other sensitive layer.

A method of identifying a side from which a radiation-recording plate has been exposed to radiation may comprise: incorporating in the plate, in a position that substantially does not interfere with an image area of the plate, a marker whose appearance in the image identifies which side the plate is exposed from; exposing the plate to the radiation; and observing the image for the identification of the side of the plate exposed. The method may further comprise: arranging the marker to indicate a rotational orientation of the plate; and observing the image for the indication of the rotational orientation of the plate. The method may yet further comprise observing the image using image processing software, the image processing software recognizing the marker and reorienting an image of the plate to have a clinically expected orientation. The method may yet further comprise: storing with the image an indication of whether the image has been reoriented by an odd number of times. The method may also comprise: substituting for the marker a replacement marker indicative of the software having processed the image; storing the image with the replacement marker. This method may also further comprise: storing with the image an indication of whether the image has been reoriented by an odd number of times.

A method of making a radiation sensitive plate having at least one radiation sensitive layer may comprise: providing a film sensitive to the radiation on a first side of the radiation sensitive plate; and applying a suspension of a heavy metal in a binder to a region of a second side of the radiation sensitive layer.

BRIEF DESCRIPTION OF DRAWINGS

The accompanying drawings are not intended to be drawn to scale. In the drawings, each identical or nearly identical component that is illustrated in various figures is represented by a like numeral. For purposes of clarity, not every component may be labeled in every drawing. In the drawings:

FIG. 1 is a perspective view of a human mandible and teeth showing how a dental X-ray plate is exposed from both the left and right sides;

FIG. 2 is a representation of an image produced by exposing a conventional digital dental X-ray plate having a "front side" facing left through the right side of the patient's mandible, scanning the image from the "front side" of the plate, and flipping the image horizontally using software;

FIG. 3 is a representation of an image produced by exposing a conventional digital dental X-ray plate having a "front side" facing left through the right side of the patient's mandible and scanning the image from the "front side" of the plate;

FIG. 4 is a representation of an image produced by exposing a conventional digital dental X-ray plate having a "front side" facing left through the left side of the patient's mandible, scanning the image from the "front side" of the plate, and flipping the image horizontally using software;

FIG. 5 is a representation of an image produced by exposing a conventional digital dental X-ray plate having a "front side" facing left through the left side of the patient's mandible and scanning the image from the "front side" of the plate;

FIG. 6 is a representation of an image produced by exposing a conventional digital dental X-ray plate having a "front side" facing left through the right side of the patient's mandible, scanning the image from the "front side" of the plate, and flipping the image horizontally;

FIG. 7 is a representation of an image produced by exposing a conventional digital dental X-ray plate having a "front side" facing left through the right side of the patient's mandible and scanning the image from the "front side" of the plate;

FIG. 8 is a representation of an image produced by exposing a conventional digital dental X-ray plate having a "front side" facing left through the left side of the patient's mandible, scanning the image from the "front side" of the plate, and flipping the image horizontally;

FIG. 9 is a representation of an image produced by exposing a conventional digital dental X-ray plate having a "front side" facing left through the left side of the patient's mandible and scanning the image from the "front side" of the plate;

FIG. 10 is a representation of an image produced by exposing a conventional digital dental X-ray plate having a "front side" facing right through the right side of the patient's mandible and scanning the image from the "front side" of the plate;

FIG. 11 is a representation of an image produced by exposing a conventional digital dental X-ray plate having a "front side" facing right through the right side of the patient's mandible, scanning the image from the "front side" of the plate, and flipping the image horizontally;

FIG. 12 is a representation of an image produced by exposing a conventional digital dental X-ray plate having a "front side" facing right through the left side of the patient's mandible and scanning the image from the "front side" of the plate;

FIG. 13 is a representation of an image produced by exposing a conventional digital dental X-ray plate having a "front side" facing right through the left side of the patient's mandible, scanning the image from the "front side" of the plate, and flipping the image horizontally;

FIG. 14 is a representation of an image produced by exposing a conventional digital dental X-ray plate having a "front side" facing right through the right side of the patient's mandible and scanning the image from the "front side" of the plate;

FIG. 15 is a representation of an image produced by exposing a conventional digital dental X-ray plate having a "front side" facing right through the right side of the patient's mandible, scanning the image from the "front side" of the plate, and flipping the image horizontally;

FIG. 16 is a representation of an image produced by exposing a conventional digital dental X-ray plate having a "front side" facing right through the left side of the patient's mandible and scanning the image from the "front side" of the plate;

FIG. 17 is a representation of an image produced by exposing a conventional digital dental X-ray plate having a "front side" facing right through the left side of the patient's mandible, scanning the image from the "front side" of the plate, and flipping the image horizontally;

FIG. 18 is a representation of an image produced by exposing a digital dental X-ray plate having a "front side" facing left and embodying aspects of the invention through the right side of the patient's mandible, scanning the image from the "front side" of the plate, and flipping the image horizontally;

FIG. 19 is a representation of an image produced by exposing a digital dental X-ray plate having a "front side" facing left and embodying aspects of the invention through the right side of the patient's mandible and scanning the image from the "front side" of the plate;

FIG. 20 is a representation of an image produced by exposing a digital dental X-ray plate having a "front side" facing left and embodying aspects of the invention through the left side of the patient's mandible, scanning the image from the "front side" of the plate, and flipping the image horizontally;

FIG. 21 is a representation of an image produced by exposing a digital dental X-ray plate having a "front side" facing left and embodying aspects of the invention through the left side of the patient's mandible and scanning the image from the "front side" of the plate;

FIG. 22 is a representation of an image produced by exposing a digital dental X-ray plate having a "front side" facing left and embodying aspects of the invention through the right side of the patient's mandible, scanning the image from the "front side" of the plate, and flipping the image horizontally;

FIG. 23 is a representation of an image produced by exposing a digital dental X-ray plate having a "front side" facing left and embodying aspects of the invention through the right side of the patient's mandible and scanning the image from the "front side" of the plate;

FIG. 24 is a representation of an image produced by exposing a digital dental X-ray plate having a "front side" facing left and embodying aspects of the invention through the left side of the patient's mandible, scanning the image from the "front side" of the plate, and flipping the image horizontally;

FIG. 25 is a representation of an image produced by exposing a digital dental X-ray plate having a "front side" facing left and embodying aspects of the invention through the left side of the patient's mandible and scanning the image from the "front side" of the plate;

FIG. 26 is a representation of an image produced by exposing a digital dental X-ray plate having a "front side" facing right and embodying aspects of the invention through the right side of the patient's mandible and scanning the image from the "front side" of the plate;

FIG. 27 is a representation of an image produced by exposing a digital dental X-ray plate having a "front side" facing right and embodying aspects of the invention through the right side of the patient's mandible, scanning the image from the "front side" of the plate, and flipping the image horizontally;

FIG. 28 is a representation of an image produced by exposing a digital dental X-ray plate having a "front side" facing right and embodying aspects of the invention through the left side of the patient's mandible and scanning the image from the "front side" of the plate;

FIG. 29 is a representation of an image produced by exposing a digital dental X-ray plate having a "front side" facing right and embodying aspects of the invention through the left side of the patient's mandible, scanning the image from the "front side" of the plate, and flipping the image horizontally;

FIG. 30 is a representation of an image produced by exposing a digital dental X-ray plate having a "front side" facing right and embodying aspects of the invention through the right side of the patient's mandible and scanning the image from the "front side" of the plate;

FIG. 31 is a representation of an image produced by exposing a digital dental X-ray plate having a "front side" facing right and embodying aspects of the invention through the right side of the patient's mandible, scanning the image from the "front side" of the plate, and flipping the image horizontally;

FIG. 32 is a representation of an image produced by exposing a digital dental X-ray plate having a "front side" facing right and embodying aspects of the invention through the left side of the patient's mandible and scanning the image from the "front side" of the plate;

FIG. 33 is a representation of an image produced by exposing a digital dental X-ray plate having a "front side" facing right and embodying aspects of the invention through the left side of the patient's mandible, scanning the image from the "front side" of the plate, and flipping the image horizontally;

FIG. 50 is a plan view of a plate adapted to receive a corner marker feature;

FIG. 51 is a plan view of the corner marker feature to be received by the plate of FIG. 50;

FIG. 52 is a bottom edge view of the plate of FIG. 50, including the corner marker feature of FIG. 51; and FIG. 53 is a plan view of a plate having a simplified marker system according to some aspects of embodiments of the invention.

DETAILED DESCRIPTION

Figure 34:
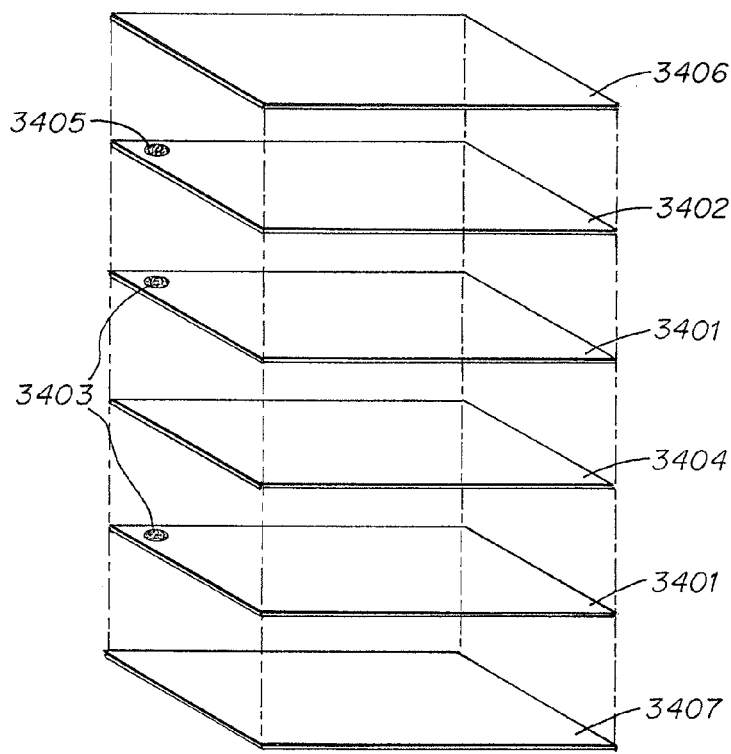
FIG. 34 is an exploded view of a laminate having radiopaque indicator marks according to aspects of the invention.

A detailed description of various aspects of embodiments of the invention follows. This invention is not limited in its application to the details of construction and the arrangement of components set forth in the following description or illustrated in the drawings. The invention is capable of other embodiments and of being practiced or of being carried out in various ways. Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

According to aspects of embodiments of the invention, exposure of one side of a radiosensitive plate produces one indicator pattern in the image, while exposure of the other side of the radiosensitive plate produces a different indicator pattern in the image. The indicator pattern recorded on the radiosensitive plate becomes a permanent part of a data pattern recorded by the particular exposure. Thus, whether the data set is embodied in the radiosensitive plate, a digital image data file, or a displayed or printed image, the indicator pattern forms a permanent part of the record. The indicator pattern may blanket the image or may be localized. It may render an image exposed through a substrate of the plate unusable, or may only minimally degrade image quality, or may be located so as not to degrade the quality of the image or data set in any way, for example by being small and located outside of a primary image forming area, such as in a corner of a rectangular plate.

Because the means for forming the indicator pattern is a permanent part of the plate, put there at the time of manufacture, no single or repetitive operator act is required to mark plates with their direction of exposure, no protocol to ensure exposure from a particular side of a plate is required, unless an indicator of a type rendering the image unusable when exposed from a "wrong side" is used, and the indication of the direction of exposure is unambiguously embedded in any data set produced from such a plate. No special protocol or specification of protective sleeves is required for image orientation purposes, either, unless an indicator of a type rendering the image unusable when exposed from a "wrong side" is used.

The indicator pattern can further be used to help identify laterality, i.e., "handedness," of an image. Preservation of the laterality of an image may be important because the symmetry inherent in the human body and most higher animal forms makes distinguishing between certain structures, such as a patient's left incisor and the patient's right incisor, difficult independently, i.e. without other sources of identification. In the case of intraoral dental radiographs, laterality is fully defined by the direction of exposure and the structure depicted. This is so because the radiation source for intraoral dental X-rays is always located outside the patient's mouth and the sensitized plate is always located within the patient's mouth.

Several different structures that produce indicator patterns having the characteristics discussed above and which unambiguously identify each of the possible transpositions are now described in detail. There are two independent non-overlapping categories of markers, "front side" markers and "back side" markers.

A "front side" marker is one that produces a mark in an image on a plate exposed from the "front side", i.e., the side from which the plate is read, while a "back side" marker is one that produces a mark in an image on a plate exposed from the "back side" and subsequently read from the "front side". In general, the marker patterns can be produced by materials having suitable patterns placed intermediate the plate sensitive layer and the source of exposing radiation. These patterns can alternatively be produced by affecting the excitation and recording the resultant phosphorescence of the phosphor during the scan process, for example, by perforating the phosphor layer or by obscuring it. For example, materials can, using any suitable process, be coated, printed, painted, laminated, sublimated, bonded, riveted, etc. onto the plate surfaces during the fabrication process. The materials can be selected to partially or wholly block or intensify, e.g. by use of different phosphor, the radiation reaching the plate in the area covered. A common material that blocks X-radiation, and can be usefully applied to plates in laminated form, in paints or in inks is lead. Other heavy metals or other heavy elements can also be used, in various forms, e.g., foils, grains, etc. of lead, tin, bismuth, barium, etc. Here, heavy metals and heavy elements generally include any element from the fourth row of the periodic table and heavier.

One example of the type of plate to which the principles of the invention are applicable is a dental plate including a plastic substrate onto which is coated a storage phosphor material sensitive to dental X-rays. The plates are produced in large sheets or continuous webs and then die-cut into their final size and shape.

A simple embodiment is now described, in which a plate such as just described, readable from one side, i.e., the "front side", has an indicator pattern-forming material, i.e., a marker, incorporated into such plate on the opposite side of the plane of the sensitive layer from which such plate is read. This is a "back side" marker.

In this embodiment, a mark is printed on the "back side", in one corner thereof. The mark is printed using a lead impregnated paint, or other suitable material. Other suitable constructions are described in greater detail, below. When exposed from the "front side" of the plate, the resulting image includes no mark. However, when exposed from the "back side" of the plate, an unexposed mark is formed in that portion of the image corresponding to the corner of the plate on which the mark is printed. The image produced, including the mark, can take the form of any of the images of FIGS. 2–33. The mark need not have any special shape because the information desired can be simply derived from the presence or absence in the image of the mark. Images produced by exposing the plate from one side or the other are distinguishable in the same manner as described below in connection with FIGS. 18, 19, 20 and 21, for example. According to this embodiment, only a "back side" marker is required in contrast to conventional media which use only a "front side" marker.

In a second embodiment, both a "front side" marker and a "back side" marker may be present. For example, different patterns of indicator-forming material may be applied to opposite sides of a plate readable from one side. Alternatively, the "front side" marker may be one or more perforations in the phosphor. This embodiment is advantageous in that the indicator pattern formed can unambiguously inform a person reading the resulting image from which direction the plate was exposed, whereas when the plate of the first embodiment is exposed from the direction that produces no indicator pattern, the image is indistinguishable from images produced by plates not including any markers or flipped horizontally.

Embodiments of the invention incorporating both a "front side" marker and a "back side" marker can fully indicate the orientation of a structure imaged, even when the position of the radiation source and the radiation sensitive plate relative to the structure is unknown.

If the plate is marked by both a "front side" marker and a "back side" marker, as described in connection with the second embodiment, the direction of exposure of the plate is unambiguously recorded in the image without any intervention or special act by the operator. In addition, the cassette or sleeve in which the plate is placed during exposure can include a radiopaque mark on one or both sides, unambiguously indicating the proper orientation of the cassette or sleeve relative to some absolute reference such as the left side or front of the patient.

FIGS. 18, 19, 20 and 21 illustrate four images that can be produced using a digital X-ray plate according to this embodiment of aspects of the invention, exposed from each of two sides, using each of two differently located sources, e.g., positioned at SOURCE L and SOURCE R. This embodiment has an open circle mark on the X-ray sensitive side of the plate, in one corner, and a filled circle mark on the other side of the plate, in this case in the same corner. In using this embodiment, attention need not be paid to which side faces the source because, as explained below, different marks appear on the image produced, depending on the side from which the plate is exposed.

Suppose, for the purpose of analyzing the images in FIGS. 18, 19, 20 and 21, that the technician, dentist or other exposing this patient's digital dental X-ray plate 104 has oriented the open circle, and consequently the sensitive side of the plate 104, toward the X-ray source located at the position SOURCE L, and in the lower right corner of the plate 104 as viewed from the direction of the X-ray source located at the position SOURCE L. In this embodiment, the filled circle is on the opposite side of the plate 104, in the same corner as the open circle. FIG. 19 is the image read from the sensitive side of the plate 104, when the plate so oriented is exposed by an X-ray source at the location designated SOURCE R. The dentist reading such an image will recognize that it was exposed from the reverse side of the plate 104 because of the presence of the closed circle 1801 and use image processing software to reorient the image by horizontally flipping the image so the filled circle 1801 appears in the expected corner of the image, as shown in FIG. 18. Note that it is known that the filled mark, as described above, is oriented to the bottom-left corner of the plate 104, and must appear in that corner when the image is properly oriented, i.e., oriented so that structures are depicted in their natural and expected orientation. Thus, it is clear that FIG. 18 represents the correct orientation of the image exposed through the back of the plate 104. The same plate 104, oriented the same way, but exposed from an X-ray source at the location designated SOURCE L, when read from the sensitive side of the plate 104, produces the image shown in FIG. 21. The image of FIG. 20 can be inadvertently produced by manipulation of the image processing software to horizontally flip the image of FIG. 21. However, it is known that FIG. 21 must be the correct orientation because the open mark is located, as described above, in the lower-right corner of the plate 104. Since FIGS. 18 and 21 are clearly and unambiguously the correctly oriented images, the technician, dentist or other person reading the images knows with certainty that the condition 203 is on the patient's right side.

Like FIGS. 18, 19, 20 and 21, FIGS. 22, 23, 24 and 25 illustrate four images that can be produced using a digital X-ray plate according to this embodiment of aspects of the invention, exposed from each of two sides, using each of two differently located sources, e.g., positioned at SOURCE L and SOURCE R. This embodiment has an open circle mark on the X-ray sensitive side of the plate, in one corner, and a filled circle mark on the other side of the plate, in this case in the same corner. In the embodiment illustrated by the resulting images in FIGS. 22, 23, 24 and 25, the marks are located in a top corner, rather than a bottom corner, as explained below. In using this embodiment, attention need not be paid to which side faces the source because, as explained below, different marks appear on the image produced, depending on the side from which the plate is exposed.

Suppose, for the purpose of analyzing the images in FIGS. 22, 23, 24 and 25, that the technician, dentist or other exposing this patient's digital dental X-ray plate 104 has oriented the open circle, and consequently the sensitive side of the plate 104, toward the X-ray source located at the position SOURCE L, and in the upper left corner of the plate 104 as viewed from the direction of the X-ray source located at the position SOURCE L. In this embodiment, the filled circle is on the opposite side of the plate 104, in the same corner as the open circle. FIG. 23 is the image read from the sensitive side of the plate 104, when the plate so oriented is exposed by an X-ray source at the location designated SOURCE R. The dentist reading such an image will recognize that it was exposed from the reverse side of the plate 104 because of the presence of the closed circle 1801 and use image processing software to reorient the image by horizontally flipping the image so the filled circle 1801 appears in the expected corner of the image, as shown in FIG. 22. Note that it is known that the filled mark, as described above, is oriented to the bottom-left corner of the plate 104, and must appear in that corner when the image is properly oriented. Thus, it is clear that FIG. 22 represents the correct orientation of the image exposed through the back of the plate 104. The same plate 104, oriented the same way, but exposed from an X-ray source at the location designated SOURCE L, when read from the sensitive side of the plate 104, produces the image shown in FIG. 25. The image of FIG. 24 can be inadvertently produced by manipulation of the image processing software to horizontally flip the image of FIG. 25. However, it is known that FIG. 25 must be the correct orientation because the open mark is located, as described above, in the lower-right corner of the plate 104. Since FIGS. 22 and 23 are clearly and unambiguously the correctly oriented images, the technician, dentist or other person reading the images knows with certainty that the condition 103 is on the patient's right side.

FIGS. 26, 27, 28 and 29 illustrate four images that can be produced using a digital X-ray plate according to this embodiment of aspects of the invention, exposed from each of two sides, using each of two differently located sources, e.g., positioned at SOURCE L and SOURCE R. This embodiment has an open circle mark on the X-ray sensitive side of the plate, in one corner, and a filled circle mark on the other side of the plate, in this case in the same corner. In using this embodiment, attention need not be paid to which side faces the source because, as explained below, different marks appear on the image produced, depending on the side from which the plate is exposed.

Suppose, for the purpose of analyzing the images in FIGS. 26, 27, 28 and 29, that the technician, dentist or other exposing this patient's digital dental X-ray plate 104 has oriented the open circle, and consequently the sensitive side of the plate 104, toward the X-ray source located at the position SOURCE R, and in the lower right corner of the plate 104 as viewed from the direction of the X-ray source located at the position SOURCE R. In this embodiment, the filled circle is on the opposite side of the plate 104, in the same corner as the open circle. FIG. 26 is the image read from the sensitive side of the plate 104, when the plate so oriented is exposed by an X-ray source at the location designated SOURCE R. The dentist reading such an image will recognize that it was exposed from the sensitive side of the plate 104 because of the presence of the open circle 201. However, the image could be inadvertently or intentionally reoriented by horizontally flipping the image so the open circle 201 appears in the lower left corner of the image, as shown in FIG. 27. Note that it is known that the open mark, as described above, is oriented to the bottom-right corner of the plate 104, and must appear in that corner when the image is properly oriented, i.e., oriented so that structures are depicted in their natural and expected orientation. Thus, it is clear that FIG. 26 represents the correct orientation of the image exposed through the sensitive side of the plate 104. The same plate 104, oriented the same way, but exposed from an X-ray source at the location designated SOURCE L, when read from the sensitive side of the plate 104, produces the image shown in FIG. 28. The image of FIG. 29 can be produced by manipulation of the image processing software to horizontally flip the image of FIG. 28, so as to locate the closed circle 1801 in the lower left corner of the image, as expected for an image produced by exposing the plate 104 from the "back side" of the plate. It is known that FIG. 29 must be the correct orientation because the closed mark is located, as described above, in the lower-left corner of the plate 104. Since FIGS. 26 and 29 are clearly and unambiguously the correctly oriented images, the technician, dentist or other person reading the images knows with certainty that the condition 103 is on the patient's right side.

Like FIGS. 26, 27, 28 and 29, FIGS. 30, 31, 32 and 33 illustrate four images that can be produced using a digital X-ray plate according to this embodiment of aspects of the invention, exposed from each of two sides, using each of two differently located sources, e.g., positioned at SOURCE L and SOURCE R. This embodiment has an open circle mark on the X-ray sensitive side of the plate, in one corner, and a filled circle mark on the other side of the plate, in this case in the same corner. In the embodiment illustrated by the resulting images in FIGS. 30, 31, 32 and 33, the marks are located in a top corner, rather than a bottom corner, as explained below. In using this embodiment, attention need not be paid to which side faces the source because, as explained below, different marks appear on the image produced, depending on the side from which the plate is exposed.

Suppose, for the purpose of analyzing the images in FIGS. 30, 31, 32 and 33, that the technician, dentist or other exposing this patient's digital dental X-ray plate 104 has oriented the open circle, and consequently the sensitive side of the plate 104, toward the X-ray source located at the position SOURCE R, and in the upper left corner of the plate 104 as viewed from the direction of the X-ray source located at the position SOURCE R. In this embodiment, the filled circle is on the opposite side of the plate 104, in the same corner as the open circle. FIG. 30 is the image read from the sensitive side of the plate 104, when the plate so oriented is exposed by an X-ray source at the location designated SOURCE R. The dentist reading such an image will recognize that it was exposed from the sensitive side of the plate 104 because of the presence of the open circle 201. However, the image could be inadvertently or intentionally reoriented by horizontally flipping the image so the open circle 201 appears in the upper right corner of the image, as shown in FIG. 31. Note that it is known that the open mark, as described above, is oriented to the upper-left corner of the plate 104, and must appear in that corner when the image is properly oriented. Thus, it is clear that FIG. 30 represents the correct orientation of the image exposed through the sensitive side of the plate 104. The same plate 104, oriented the same way, but exposed from an X-ray source at the location designated SOURCE L, when read from the sensitive side of the plate 104, produces the image shown in FIG. 32. The image of FIG. 33 can be produced by manipulation of the image processing software to horizontally flip the image of FIG. 32, so as to locate the closed circle 1801 in the upper right corner of the image, as expected for an image produced by exposing the plate 104 from the "back side" of the plate. It is known that FIG. 33 must be the correct orientation because the closed mark is located, as described above, in the lower-left corner of the plate 104. Since FIGS. 30 and 33 are clearly and unambiguously the correctly oriented images, the technician, dentist or other person reading the images knows with certainty that the condition 103 is on the patient's right side.

Figure 39:
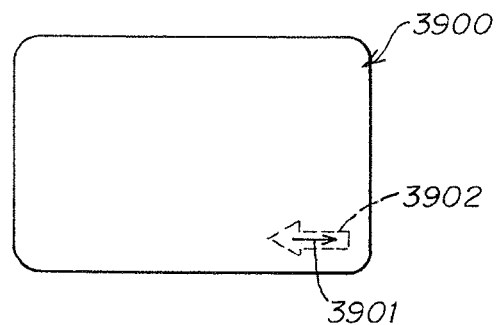
FIG. 39 is a plan view of a plate showing the relative positions of a "front side" marker (solid) and a "back side" marker (phantom)

In a third embodiment of the invention, shown in FIG. 39, the markers are asymmetric, are asymmetrically placed with respect to the plate surface axes of symmetry, and both "front side" and "back side" markers are employed. In the example, the markers 3901 and 3902 are made in the shape of arrows. Of course, markers 3901 and 3902 could be any suitable directional marker meeting the further requirements described in connection with this embodiment. Let us further suppose that the "front side" marker 3901 is a thin, short, horizontally directed arrow pointing at the right vertical edge of the plate at the lower edge of image 3900, while the "back side" marker 3902 is a solid arrow, also horizontally directed at the lower edge of a "landscape" oriented plate, but pointing away from the vertical edge of the plate of image 3900. For purpose of illustration, by virtue of their size and placement on the opposite sides of plane defined by the plate, the relationship between the markers 3901, 3902 produces an overlap between the image of the two markers. In this particular arrangement, when the plate is exposed from the "back side" and then scanned, the two arrows overlap producing an image of the larger solid arrow of the "back side" marker on the plate image and obscuring the thinner "front side" marker. Thus, only one arrow shows in any exposed and scanned plate image.

Figure 38:
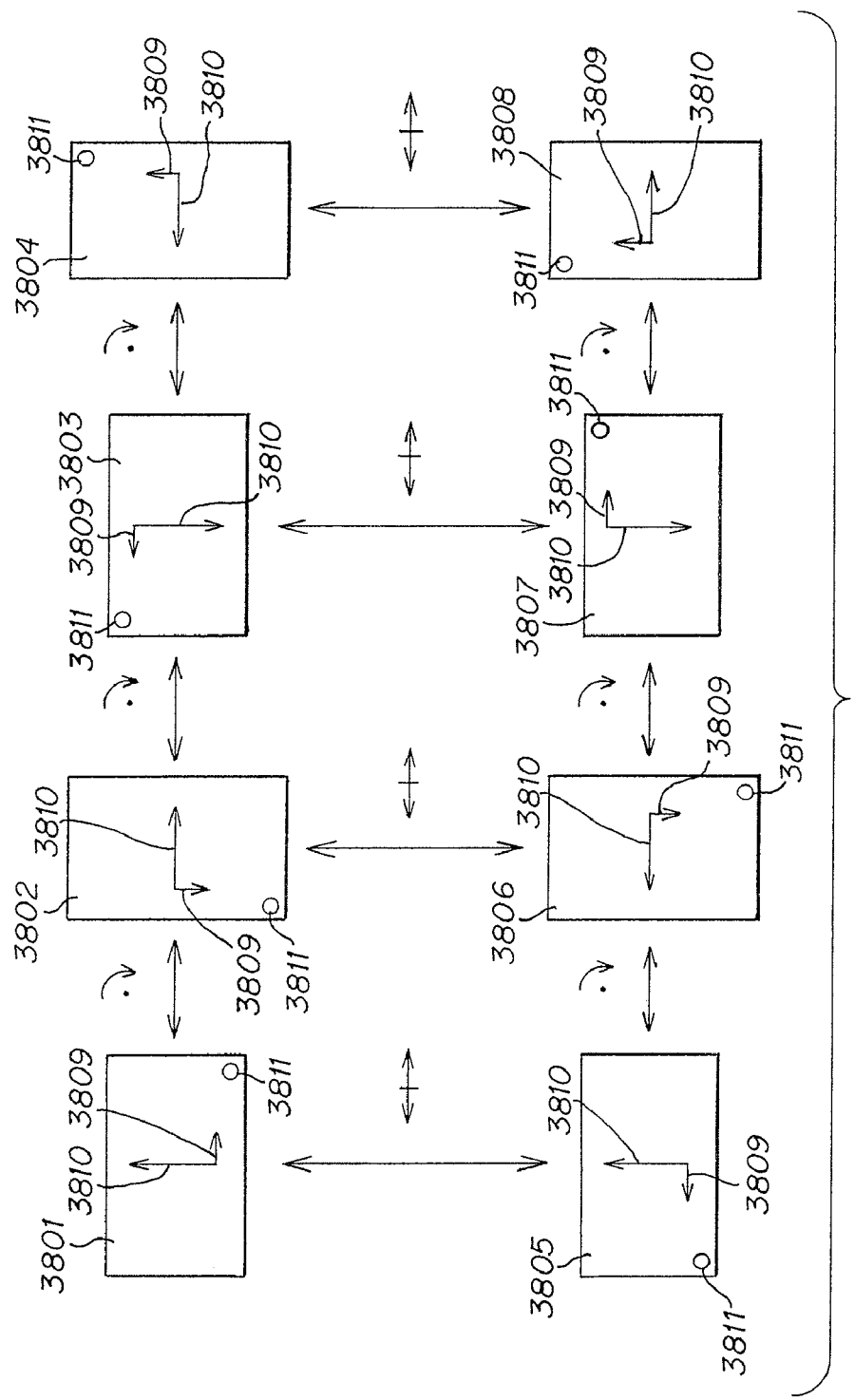
FIG. 38 is a transposition map illustrating the relationships between various transpositions of an image.

In extending the method of analysis used in the discussion relating to FIG. 38 to this third embodiment of the invention, all possible landscape images that can be produced with exposure from the "front side" and then manipulated through the plane rotations and reflections described earlier are illustrated in FIG. 40. In the interest of simplicity of the illustration only "landscape" orientation of the image need be discussed presently: By virtue of the relative ease in finding the superior-inferior orientation, it is for practical reasons nearly impossible to confuse two, intraoral dental images, as well as images of many other anatomical structures, which are related to each other by a rotation of ninety degrees because a horizontal image and a vertical image have teeth aligned either with the short or the long axis of the plate, an easily discriminated condition. Furthermore, the different orientations of the plate are typically used in different applications. "Portrait" orientation is generally used with anterior tooth periapical and also vertical bitewing studies, whereas "landscape" orientation is used with posterior tooth periapical and also horizontal bitewing studies. Also, it has been already demonstrated earlier in the discussion regarding FIG. 38 relative to "landscape" oriented images, that this method of analysis can be extended to and is valid for "portrait" oriented images.

Figure 40:
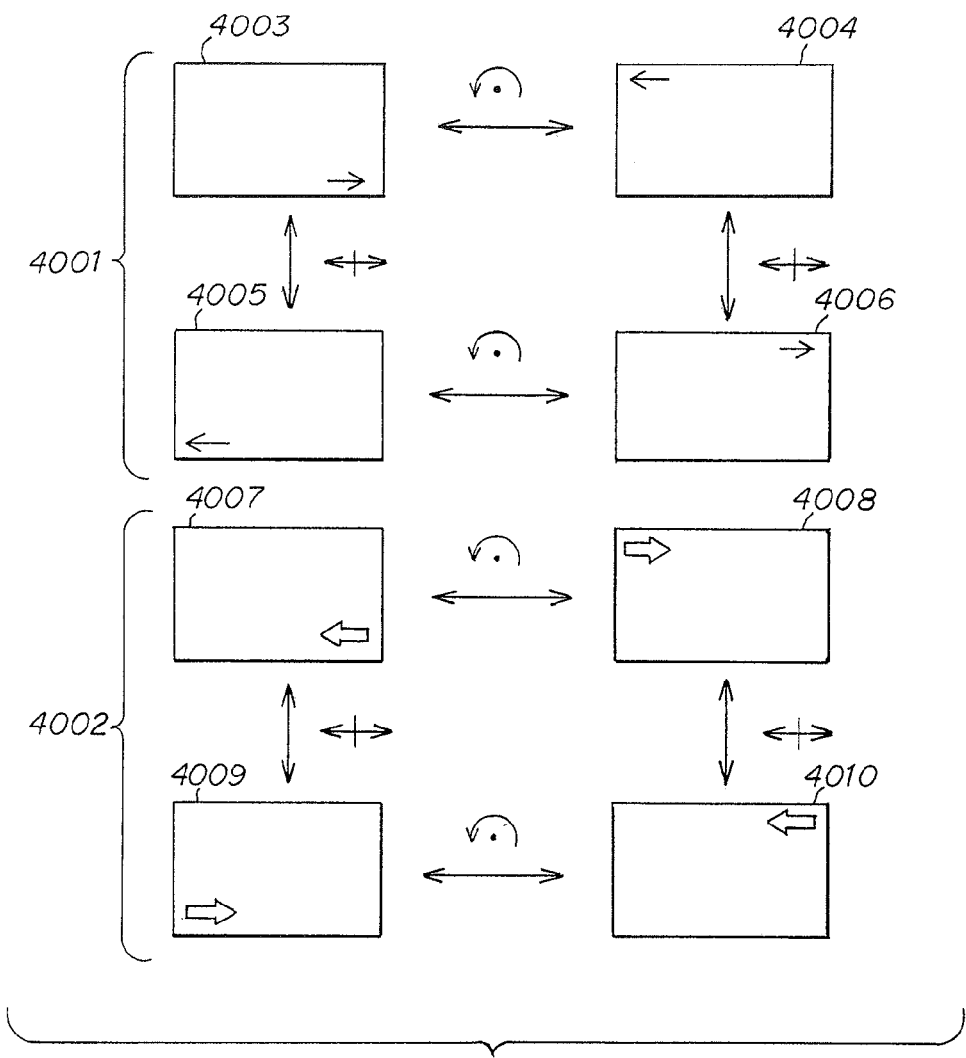
FIG. 40 is a transform map of the plate of FIG. 39.
Figure 42:
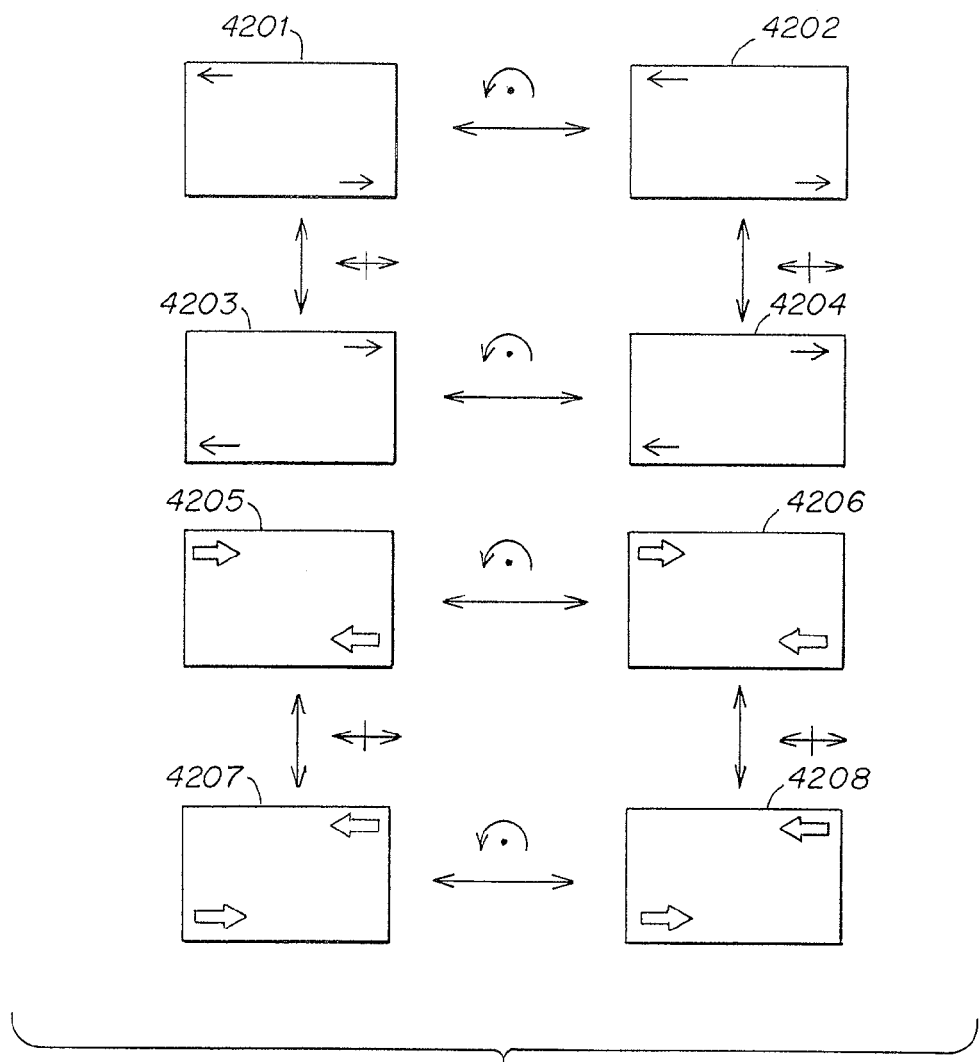
FIG. 42 is a transform map of the plate of FIG. 41.

The following discussion of FIG. 40 extends the method of analysis applied regarding FIG. 38 to the third embodiment of the invention. The two motions, a 180 degree rotation around an axis perpendicular to the plane of the plate (or the image) at the intersection of its long and short axis, and a reflection through a vertical plane perpendicular to the plane of the image, are the four modes of manipulation which, singly or when combined, produce all allowed orientations of the image.

The first mode is "pre-exposure" reflection of the plate, changing whether the plate is exposed from the "front side" or from the "back side". Depending on which initial reflection position a plate has been exposed in, one of group 4001 and 4002 will be the starting point of analysis.

The second mode of manipulation is a physical rotation of the plate prior to exposure involved in changing the orientation from "portrait" to "landscape", and if continued, back to "landscape", and which changes the relationship between the location of the marker and details of the image produced by the shadow-gram. As has been demonstrated in the discussion regarding FIG. 38 and FIGS. 2 through 33 there exists equivalence between the two possible orientations attainable through this mode within the "landscape" orientation, and by extension also within the "portrait" orientation; therefore, further discussion of this manipulation will be deferred after stating that this rotation mode produces an effect on an asymmetric, or asymmetrically placed, marker which is equivalent to a reflection through a point located at the intersection of the plate's long and short axis of symmetry. Which initial exposure rotation has occurred determining whether the starting point for analysis of an image will be in the left column of images or the right column of images in FIG. 40.

The third mode, a rotation of the plate after exposure, when mounted into the scanner or by software once the data has been captured, maintains the relationship between the location of the marker and the details of the shadow-gram. As discussed below, this mode is illustrated by movements between the left and right columns of FIG. 40. This mode is referred to as "post-exposure" rotation.

The fourth mode is software reflection of the image after capture. This manipulation is illustrated in FIG. 40 by vertical movement between rows, while remaining within the original group 4001 or 4002.

A plate having "front side" markers and "back side" markers, exposed from an arbitrary side and then manipulated by image processing software will produce one of the images of FIG. 40, as noted above. Analysis of those images is discussed below in connection with four hypothetical starting points 4003, 4004, 4007 and 4008.

Hypothetical #1

An image scanned from a plate exposed in the conventionally "correct" orientation, that is, with the "front side" marker facing the source of radiation and at the lower edge is shown in image 4003. Software manipulations by rotation or reflection can produce any of images 4004, 4005, or 4006 in group 4001. However, note that the thin, "front side" marker arrow is at the lower edge facing right when the image 4002 is correctly oriented.

Hypothetical #2

An image as scanned from a plate exposed from the "front side", but rotated so that the "front side" marker is at the upper edge producing the scanned image 4004. Again, software manipulation can produce any of the images 4003, 4005 and 4006. When correctly oriented for viewing, this image 4004 has the thin, "front side" marker arrow at the upper edge facing left.

Hypothetical #3

According to this hypothetical, the plate is exposed from the "back side", with the "back side" marker in the lower edge. When scanned, image 4007, with the "back side" marker on the lower right, facing left is produced. Because this image was subject to a pre-exposure reflection, the scanned image 4007 is produced. A software reflection produces the correct image 4009. Although images 4008 and 4010 could also be produced by software manipulation, observe that "correct" image 4009 has the thick, "back side" marker arrow at the lower edge facing right.

Hypothetical #4

According to this last hypothetical, the plate is exposed from the "back side" after being rotated so that the "back side" marker is at the upper edge, producing scanned image 4008. In order to view the image in a "correct" orientation, it is manipulated using software to reflect horizontally the image 4008, to produce image 4010. The corrected image 4010 has the thick, "back side" marker arrow at the upper edge facing left.

A simple rule can be derived from the four foregoing hypothetical using aspects of the third embodiment, whereby any image produced using the embodiment can be quickly and accurately oriented correctly for viewing. For landscape mode images, after orienting an image correctly with respect to superior/inferior parts using rotation, any marker arrow at the top edge of the image should point left, any marker arrow at the bottom edge of the image should point right. The image must, using software, be reflected horizontally to achieve correct orientation if the rule is not met initially.

Figure 41:
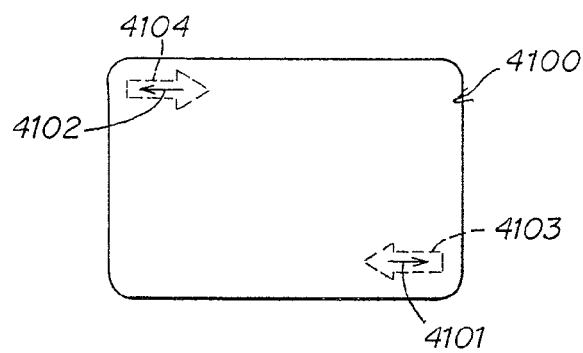
FIG. 41 is a plan view of a plate showing the relative positions of dual "front side" markers (solid) and dual "back side" markers (phantom)

In a fourth embodiment of the invention, illustrated in FIG. 41, two "front side" 4101, 4102 and two "back side" markers are used in the following manner. The relationship between markers 4101, 4103 and 4104 is similar to that described in connection with markers 3901 and 3902 of the third embodiment. However, a second set of markers 4102, 4104 bearing a similar relationship is located at the point of reflection of the first set through a line passing perpendicularly through the center of the face of the plate.

All the possible images 4201–4208 generated by scanning such a plate exposed to a radiation source from the "front side" and from the "back side" are shown in corresponding positions to those of FIG. 40. The arrows associated with the properly oriented images all point to the right if they are in the lower half of the image and to the left if the are in the upper half of the image, making the rule stated above even easier to apply. Such design of the marker shape and location in the processed image facilitates not only accurate and unambiguous orientation but also further reduces the number of decisions that an operator must make in the process of arranging the images in the mount, thus reducing the time required for the operation.

Furthermore, even if one of the markers should be obscured by the shadow of a clinical structure which is radiopaque, e.g., a metallic filling or crown, the other is present to even in this rare situation provide indication of the laterality of the image.

In a yet another embodiment of the invention, the plate is fitted with two layers of sensitive material, each possessing a small "front side" marker and allowing the mechanism which converts the latent image into a visible diagnostic image to read the plate from either or both sides and producing a recognizable pattern of that marker in such a diagnostic image, and a different indicator-forming marker or material, housed between the two sensitive layers, capable of producing a recognizable pattern, preferably obscuring the image of the "front side" marker as in the foregoing embodiment, readable from either of the sensitive layers if such material lies between a radiation source and that layer.

Figure 44A:
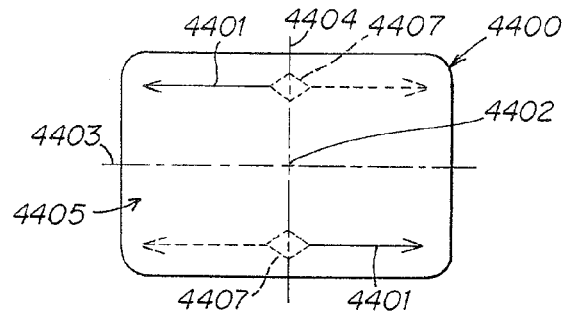
FIG. 44 is a plan view of a double-phosphor plate showing the relative positions of a "front side" marker (solid arrow, phantom arrow) and a "back side" marker (phantom diamond) when viewed from either side, and representing exposure and viewing from the same side.
Figure 44B:
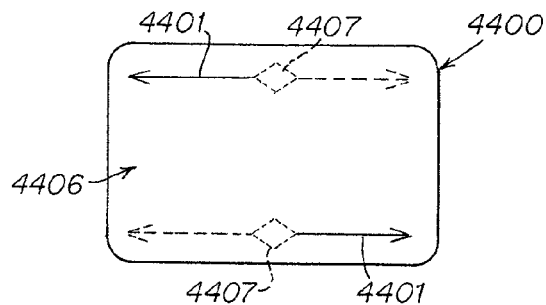

An example of aspects of this embodiment is shown by the plate 4400 illustrated in FIG. 44. The "front side" marker set is comprised of two pairs, one pair on each side, of two arrows 4401, arranged on the plate in the following manner: each arrow, lying along and near a long edge of the plate, originates near the midpoint of the nearest long edge and points toward the right short edge if it is located near the lower long edge, or toward the left short edge if lying near the upper long edge. The same arrangement of arrows is present on the reverse side of the plate. The two arrows reflect onto one another through the point of intersection 4402 of the long 4403 and the short 4404 axes of symmetry of the plate as represented in FIG. 44. The resulting "front side" marker configuration is such that the two sides 4405 and 4406 of the plate are indistinguishable from one another, both having phosphor coating and arrows which lie in identical positions relative to one another through any manipulations that preserve the "landscape" or "portrait" orientation of the plate 4400, i.e. any 180 degree or multiple thereof, rotation about any of the principal axes 4403 and 4404 of symmetry or the point 4402 of symmetry.

Figure 45:
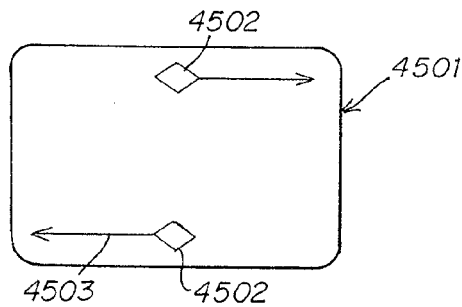
FIG. 45 is a plan view of an image produced by a double-phosphor plate showing the relative positions of the "front side" marker and the "back side" marker when exposed from one side and viewed from the other side, after the image has been flipped horizontally.

According to further aspects of this embodiment, between the two phosphor film layers lie near the tail ends of each of the four arrows 4401, radiopaque medium deposits 4407 which can cast a shadow onto the phosphor on the side of the plate opposite the source of radiation and the radiographed object. In the landscape orientation (as shown), the above arrangement of arrow-shaped "front side" markers 4401 and internal material 4407 comprising a "back side" marker, any image of an object exposed from and read from the same side of the plate will have proper orientation, as always, as scanned, with the lower edge arrow 4401 pointing to the right and the "back side" marker 4407 shadow absent. On the other hand, as shown in FIG. 45, any image 4501 of an object exposed from one side of the plate and read from the other will reveal the "back side" marker image 4502, which will appear at the right side, i.e. the tail, of the lower arrow 4503 when the diagnostic image has been properly oriented by the software. An image with the lower arrow (FIG. 44, 4401) pointing right in the absence of the "back side" marker shadow has also been properly oriented. However, an image (not shown) with a "back side" marker shadow present at the left end, i.e. the tail, of the "front side" marker would indicate an image in which right and left are reversed and requiring software reflection for proper orientation of the diagnostic image. As with the previous embodiments similar analysis generates simple rules for proper image orientation.

As seen from the above discussion, plates according to the various embodiments described produce images with distinctive markers permanently embedded in the image information. The distinctive markers can be recognized and acted upon by the dentist or technician viewing the images, or can be automatically recognized and acted upon by the image processing software used to view the images. More sophisticated software can first perform the superior/inferior orientation on its own, based on any suitable image processing rules, while less sophisticated software can rely on the operator to first perform the superior/inferior orientation. In order to effect automatic orientation recognition and reorientation, the image processing software would next search the known possible locations of the markers for those particular shapes corresponding to the markers. When one of those shapes is found in one of those possible locations of the markers, a rule for correctly orienting the image is then applied. In the case of the third or fourth embodiments described above, the simple rule set forth above can easily be applied automatically by the software to bring each image immediately into its correct orientation. The software can also be written to replace a marker recognized within an image with one of its own. The substitution would help those using the images recognize that they have been processed and correctly oriented.

Another software enhancement is also possible in connection with aspects of embodiments of the invention. The reflection process performed by the image processing software can modify the file by toggling a "reflection flag" indicative of whether the image has been reflected an odd or even number of times. The reflection flag can be embedded within the image file, can be stored in an independent file, can be part of the image file name, or stored in any other suitable location. The value of the reflection flag can represent one of two states. The reflection process and reflection flag would preferably satisfy the following conditions:

1. The reflection process flips the reflection flag state from one to the other, each time a reflection was applied to a given image, thereby tracking the number of reflections, modulo two;

2. The image file so processed is modified to include a graphic, text or other indication, that the image has been reflected horizontally (through a vertical axis of reflection); and 3. The repeated use of the reflection tool would toggle the reflection flag between the two states each time it is used.

The image processing system would display a correctly oriented image either if the "back side" marker were present and the reflection flag were indicating an odd number of reflection operations, or if the "back side" marker were absent and the reflection flag indicated an even (including zero) number of reflection operations.

Plates embodying aspects of the invention can be manufactured by any suitable method. The mark to be produced can be of any arbitrary size relative to the size of the plates to be produced. In production methods in which one or more plates are cut from larger sheets or webs of material coated on one side with phosphor or another radio-sensitive material, placement of the mark can be synchronized with the locations from which the plates are cut, may be randomly placed relative to the locations from which the plates are cut, or may completely blanket the locations from which the plates are cut. Synchronization can be achieved by any suitable method, including those known in the printing arts for aligning printed elements and die cuts.

A small, highly distinctive mark can be placed in a consistent, predetermined location, whereas a blanket pattern used as the mark should also be highly distinctive, so as to the distinguish it from patterns likely to be seen in the diagnostic image. Preferable blanket patters are rectilinear or angular, rather than mottled, curved or random, so as to be distinguishable from naturally occurring patterns in the diagnostic image.

As noted above, production of the mark or pattern on the plate can be done using any suitable means of varying the transmission or absorption of the diagnostic radiation.

For example, the substance of the plate which carries the phosphor might be manufactured in such a way that its absorption of the radiation which produces the latent image in the phosphor is not uniform. The non-uniformity can take the form of the desired mark or pattern. Examples of processes capable of producing the desired non-uniformity are now described.

Alternatively, also as noted above, production of the mark or pattern can be done by varying the output of an exposed plate, for example by varying the phosphor type, thickness or presence.

The pattern can be an integral part of the bulk substance of a plate having a non-uniform composition. This can be accomplished by the introduction of a material which would locally increase the extinction coefficient of the radiation and produce a recognizable pattern in the shadow cast on the phosphor when exposed from its side of the phosphor. During manufacture, a radio-opaque material, e.g. heavy metal salt powder of an appropriate particle size, can be added to the material from which the plate is formed. This addition can be performed in such way that the material would not become homogeneous prior to the finishing of the plate for example while the materials are in a semi-flowable state, before hardening into finished sheets.

The pattern can be introduced during the manufacturing of the plate as a modification of the sheet which holds the phosphor of the finished plate. Examples which can be combined as desired, include to hot press, adhere, stamp, print with ink or foil, spray, re-sublimate, dust, inlay, or otherwise deposit, or impress into, the sheet a material of different extinction coefficient than the bulk material of the sheet. This would introduce a recognizable pattern into the shadow cast onto the phosphor when exposed from its side.

As shown in FIG. 34, the sheet from which the plate is made may be a laminate or sandwich structure in which at least one layer 3401 is capable of casting a non-uniform shadow onto the phosphor 3402. That layer 3401, for example, might be a metallic foil cutout providing the label pattern 3403. Alternatively, the non-uniform layer might be obtained by one of the other methods, above which is then laminated into a finished structure. The layer 3401 is applied to one side of a substrate 3404, while the phosphor layer 3402, with a material 3405 casting a non-uniform shadow thereon, is applied to the other side of the substrate 3404. Protective layers 3406 and 3407 are applied to the outer surfaces of the structure. One potential advantage of this approach is that a method of deposition which might be inappropriate because of instability, e.g. mechanical or chemical, of the radiopaque deposit might become acceptable by sealing the deposited material inside the sandwich, thereby making it stable between the layers. Another advantage is that an otherwise convenient material which, because of undesirable properties such as toxicity, might be excluded from consideration as a surface coating, might be useable if present only in small amounts, safely sealed within the structure of the plate. Such materials might be powders, inks, or foils containing heavy metals, elements, their alloys, compounds or salts.

Figure 35:
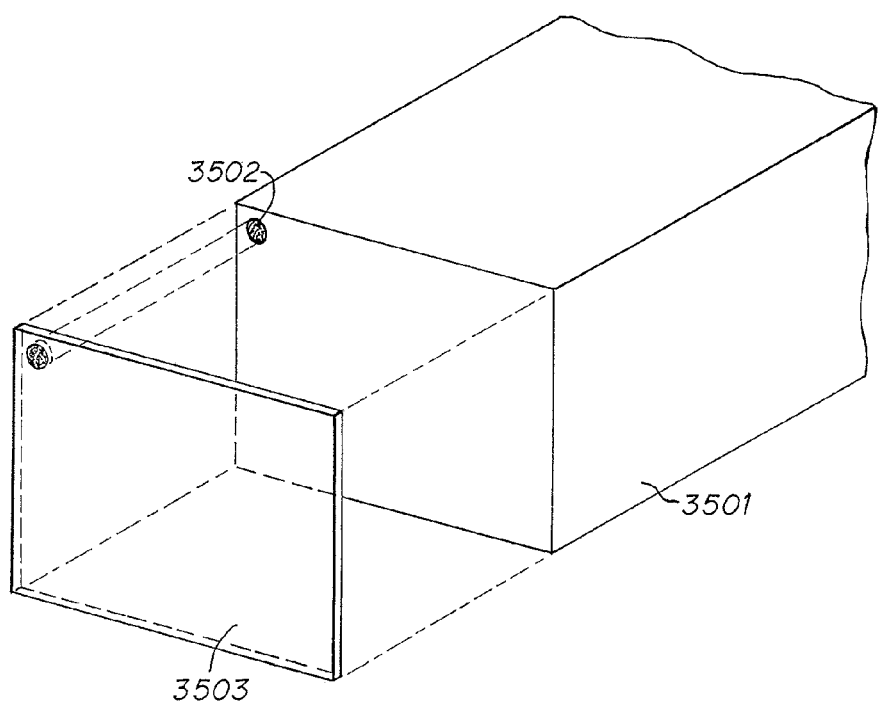
FIG. 35 is a perspective view of a bulk material having an inlaid radiopaque material and a slice cut off of the bulk material, wherein the slice can be used in constructing a digital X-ray plate according to aspects of the invention.

Another method for producing zones of contrasting radiopacity within the plate is to inlay the substrate of the plate with a full or partial thickness of material possessing a significantly different coefficient of extinction at relevant wavelengths. One way to create a full thickness inlay of this type, as shown in FIG. 35, is by transversely sectioning a non-homogeneous extrusion block 3501, having embedded therein a material 3502 capable of casting a non-uniform shadow onto the phosphor (FIG. 34, 3402, for example), where each transverse section 3503 is thin enough to be used as an individual plate.

Figure 36:
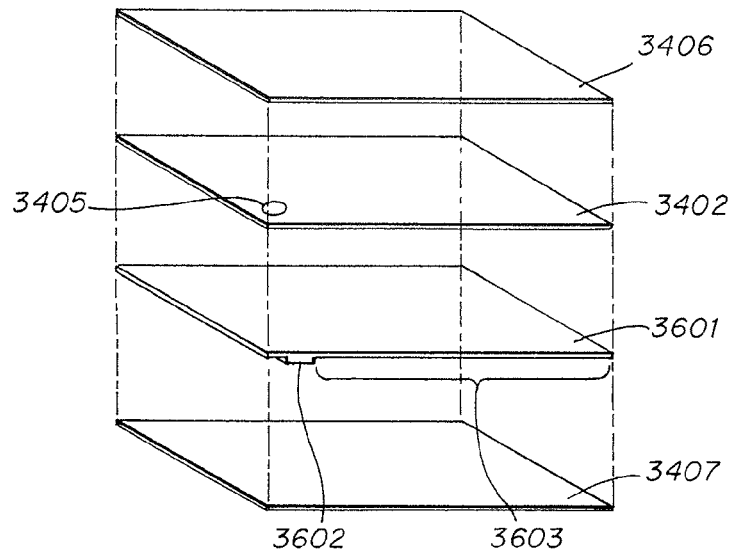
FIG. 36 is an exploded view of a radiographic plate produced using a radiopaque substrate whose thickness is varied to produce a unique marker when exposed through the substrate.

According to another structure, shown in FIG. 36, the plate is made of a material which itself has a substantial degree of radiopacity, the variation in the intensity of the shadow cast by the plate when exposed from one side might also be produced by varying the thickness of the substrate 3601 onto which the phosphor is deposited. The substance of which the plate is made would, in this example, need to possess a significant extinction coefficient for the wavelength of radiation used in the exposure. For a substrate including, for example, a heavy metal, a thick region 3602 would cast a more intense shadow than a thinner region 3603. To protect a patient from heavy metal exposure and to improve durability, protective layers 3406 and 3407 are also included.

Figure 37:
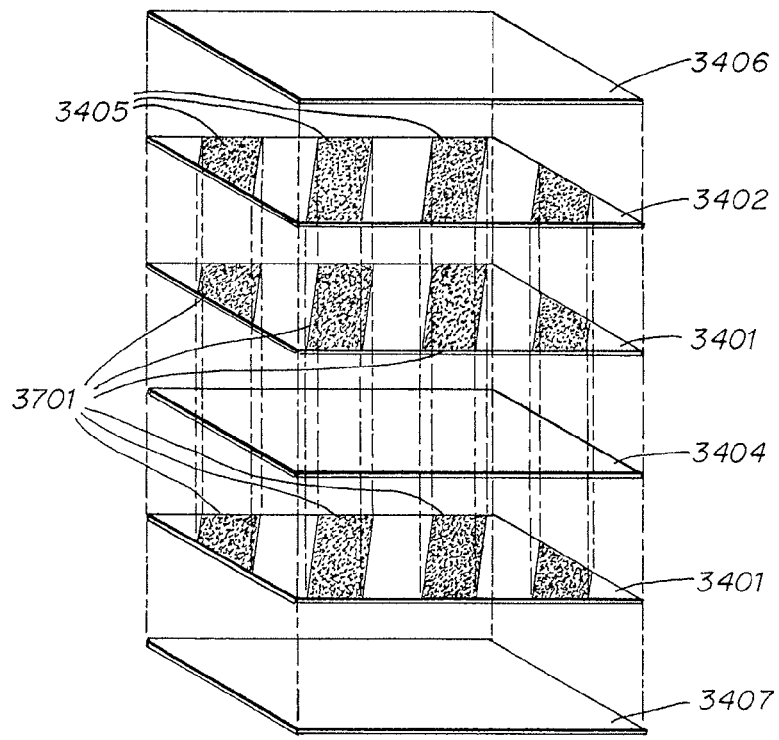
FIG. 37 is an exploded view of a radiographic plate having a radiosensitive material toward a "front side" and having toward a "back side", thereof, a radiopaque material having a pattern rendering an image exposed through the radiopaque material unusable.

According to yet another construction, as shown in FIG. 37, the mark or pattern, when the plate is exposed in an incorrect orientation, i.e. through the "back side", can be such as to cast a shadow onto the phosphor clearly warning the reader of the radiograph that the plate was exposed from the "wrong" side. The pattern 3701 and its intensity could render such an image unreadable, necessitating repetition of the exposure in a prescribed manner, i.e., with the phosphor facing the radiation source. This construction of plate and mark or pattern would be an improvement on the current phosphor plate technology in that it would eliminate any ambiguity as to the anatomical location of the source of the image recorded by the phosphor. Another advantage of this structure is that conventional dental film packets produce a similar result; hence, the dental profession is accustomed to such an approach. Such a disruptive label would, however, necessitate re-exposing the patient to ionizing radiation, when an exposure is improperly made, rather than simply indicating that the exposure was made from reverse side of the plate and permitting the reader to subsequently manipulate the image to have its usual orientation.

Figure 43:
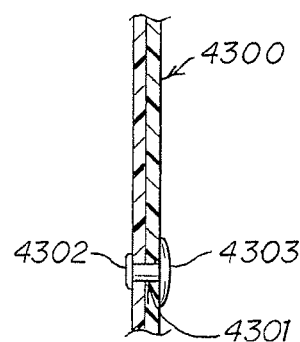
FIG. 43 is a cross-sectional view of an aspect of an embodiment of the invention using a rivet or brad to form both a "front side" marker and a "back side" marker.

According to yet another embodiment, illustrated in cross-section in FIG. 43, a small rivet, staple, brad or the like 4301, optionally holding the structure of the plate 4300 together, can serve as both a "front side" marker and a "back side" marker. Accordingly to aspects of this embodiment, the head 4302 of the rivet, staple, brad or the like 4301 can provide the "front side" marker, while the larger, spread foot 4303 of the rivet, staple, brad or the like 4301 can provide the "back side" marker. It should be understood that the roles of the head 4302 and foot 4303 of the rivet, staple, brad or the like 4301 can also be varied.

Figure 46:
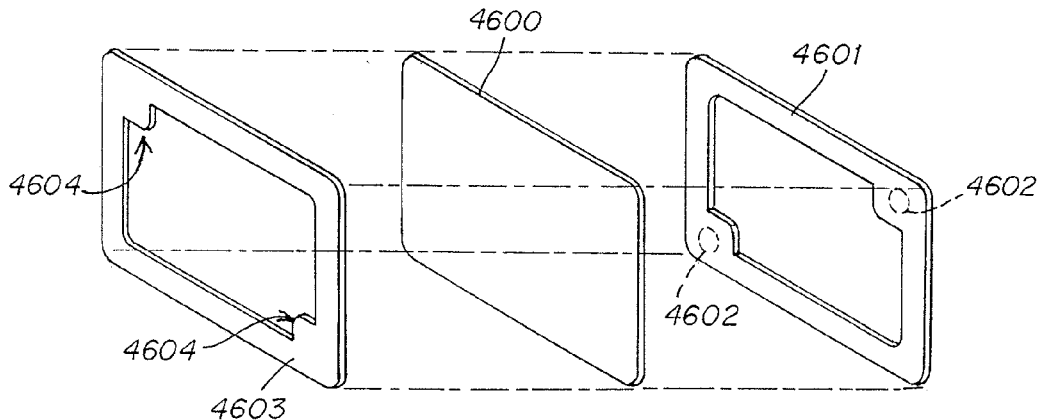
FIG. 46 is an exploded perspective view of a plate according to aspects of an embodiment of the invention including at least one frame applied to the plate.

According to yet another construction, as shown in FIG. 46, the mark or pattern-producing mass of radiopaque material 4602 can be contained or embedded within a matrix 4601 which then itself is affixed to the location on the plate 4600 chosen to demonstrate exposure from the indicated aspect of the sensitive layer in the image. As shown, the matrix can be, for example, a plastic frame 4601. The radiopaque material 4602 produces the "back side" marker, in this example. The frame 4602 can be constructed to provide compatibility with existing plate processing systems. Also, as shown, a second frame 4603 can be configures to produce a "front side" marker, as well. In this example, the "front side" marker produces an areas which cannot be read because it is blocked by a portion 4604 of the frame 4603. Such matrix 4601, 4603 can be chemically bonded, solvent welded, ultrasonically welded, directly molded onto, mechanically attached, or otherwise affixed to the plate 4600 so as not to interfere with the operation of the mechanism used for converting the latent image into visible form.

A variation on the embodiment of FIG. 46 is shown in FIGS. 50, 51 and 52. In this variation, the "frame" is not really a complete frame that surrounds the image area, but rather abbreviated to occupy only a corner (or, optionally, another small area out of the main image area) of the plate 5000. The parts of this embodiment are now described in detail.

Plate 5000 has a corner region 5001 with two voids 5002 and 5003 formed therein. The voids 5002 and 5003 are positioned, sized and shaped to retain the corner element (FIG. 51, 5100) to the plate 5000.

As shown in FIG. 51, corner element 5100 has two retaining studs 5101 and 5102, positioned, sized and shaped to fit in the voids 5002 and 5003 of plate 5000. Also, embedded within the material of which corner element 5100 is formed is a shaped body 5103 of radiopaque material. The body 5103 of radiopaque material serves the function of the "back side" marker, while the shapes of the tops of studs 5101 and 5102 serve the function of the "front side" marker.

For completeness, FIG. 52 shows the corner element 5100 attached to the plate 5000, in a bottom edge view.

According to a simplified embodiment, shown in FIG. 53, a plate 5300 has a pair of "front side" markers 5301 and a pair of "back side" markers 5302. If only the "front side" markers 5301 appear, then the resulting image indicates by the corners in which the "front side" markers appear whether it has undergone post-exposure reflection. If both the "front side" markers 5301 and the "back side" markers 5302 appear, then the resulting image was exposed from the opposite side from which it was read, i.e., it underwent pre-exposure reflection. There is insufficient information in the image, alone, to determine whether that reflection has been corrected by a subsequent post-exposure reflection. However, as described elsewhere, herein, software can replace the markers in the image with markers designed to permanently indicate the correct direction. This simplified embodiment works equally well with material that must be read only from the "front side" and material that can be read from either side.

Figure 47:
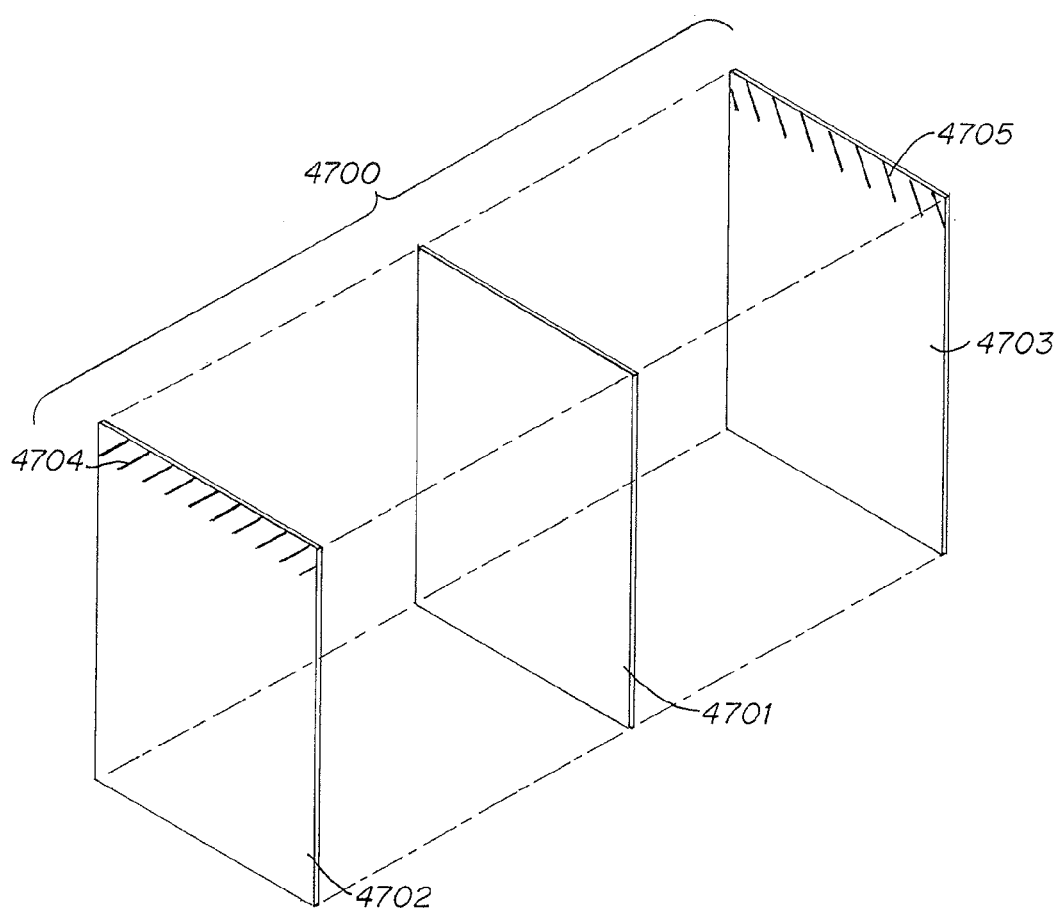
FIG. 47 is an exploded perspective view of a plate having a transparent substrate and protective layer, so that the plate can be read from either side.
Figures 48, 49:
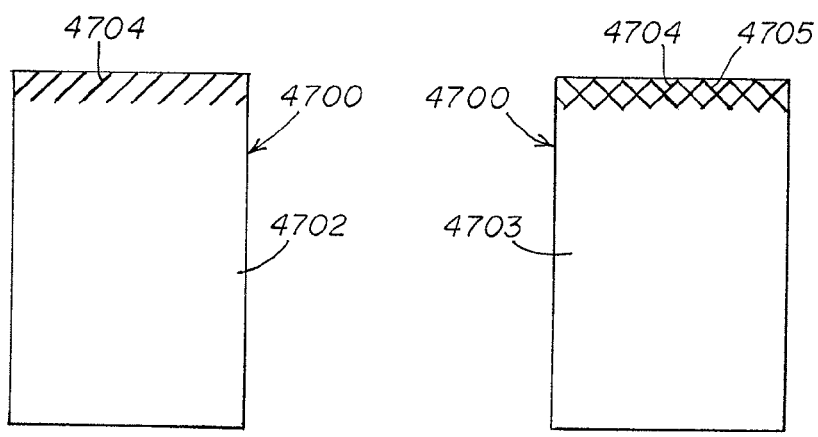
FIG. 48 is a plan view of an image produced by the plate of FIG. 47 which has been exposed from and read from the same side.
FIG. 49 is a plan view of an image produced by the plate of FIG. 47 which has been exposed from one side and read from the other side.

As shown in FIG. 47, aspects of the invention can be embodied in a plate 4700 having a phosphorescent, radiation sensitive layer 4701 and two transparent layers 4702 and 4703. One or the other of the two transparent layers 4702 and 4703 can be considered to be a substrate layer providing mechanical support for the structure, or a separate, transparent substrate layer (not shown) can be used. Transparent layers 4702 and 4703 could, in fact, be omitted, provided another substrate layer is provided, and radiopaque patterns 4704 and 4705 are provided to each side of layer 4701, for example by overprinting. Each transparent layer 4702 and 4703 should be functionally transparent to both the excitation wavelength and the phosphorescence wavelength of the radiation sensitive layer 4701. In addition to functional transparency, the layers 4702 and 4703 should exhibit low enough dispersal to be suitable for the resolution required by the application for which the plate is to be used. Each transparent layer includes at an edge a radiopaque pattern 4704 and 4705. Patterns 4704 and 4705 are selected for several qualities. They may, as in this example, be the same pattern, when each is viewed from the side of the radiation sensitive layer 4701 on which the pattern is disposed. The patterns 4704 and 4705 should be inherently asymmetrical when the plate is exposed and viewed from the same side, as shown in FIG. 48, so that a horizontal or vertical reflection of the pattern is readily apparent in the resulting image. The patterns 4704 and 4705 should combine, when exposed from one side and viewed from the other side to produce a unique pattern different from that shown in FIG. 48, as shown in FIG. 49.

When an image as shown in FIG. 48 is read from a plate, the operator can immediately discern that the image is correctly oriented. Indeed, if the image is inadvertently horizontally reflected, the pattern identifies the incorrect orientation, which can then be corrected.

When an image as shown in FIG. 49 is read from a plate, the operator (or the software performing the reading of the plate and storing of the image) can immediately discern that the image is reversed due to having been exposed from one side and read from the other. The image can then be reflected horizontally and the pattern shown in FIG. 49 can be replaced with the patter shown in FIG. 48, thus permanently embedding in the image an indication of its correct orientation.

Markers according to various aspects of embodiments of the invention described above can be made by casting low-melt temperature compositions or alloys into suitable shapes in a plate. Low temperature alloys, including eutectic alloys of Sn, Sb, Bi, Pb and/or others are suitable.

Although described in connection with digital intraoral dental plates, it should now be evident that various aspects of embodiments of the invention can be applied to other medical and dental plates or films susceptible to exposure from either side, but which can only be read or scanned from one side.

Having thus described several aspects of at least one embodiment of this invention, it is to be appreciated various alterations, modifications, and improvements will readily occur to those skilled in the art. Such alterations, modifications, and improvements are intended to be part of this disclosure, and are intended to be within the spirit and scope of the invention. Accordingly, the foregoing description and drawings are by way of example only.

What is claimed is:

1. A radiation-recording plate constructed and arranged to have a capacity to form an image of an object upon exposure to radiation impinging on the object and then incident upon the plate from a front side and to have a capacity to form an image of the object upon exposure to radiation impinging on the object and then incident upon the plate from a back side, the plate including prior to exposure a marker that produces a mark detectable in the image after exposure to radiation incident upon the plate from only one of the front side and the back side without constraint as to which, and indicative of both from which of the front side and the back side the plate is exposed to the radiation and indicative of any mirroring transformations performed upon an image recovered from the plate after exposure to the radiation.

2. The plate of claim 1, the marker comprising a medium opaque to the radiation impinging on the object and then incident upon the plate, and the marker covering a region that does not interfere with a region of interest of the image when the plate is exposed from either side.

3. The plate of claim 2, sensitive to X-radiation, the medium comprising one of a heavy element, an alloy including a heavy element, a compound including a heavy element or a salt of a heavy element.

4. The plate of claim 3, the heavy element being one of Pb, Sn, Bi, I and Ba.

5. The plate of claim 2, sensitive to X-radiation, the medium suspended in a binder applied to the region.

6. The plate of claim 1, the marker having asymmetry about at least one axis.

7. The plate of claim 6, wherein the marker has horizontal asymmetry about a vertical axis relative to a normal image orientation.

8. The plate of claim 6, wherein the marker has vertical asymmetry about a horizontal axis relative to a normal image orientation.

9. The plate of claim 1, the marker further comprising a back side marker producing a mark in the image whose appearance in the image on the plate indicates exposure from the back side without interfering with a region of interest of the image.

10. The plate of claim 9, wherein the marker is a rivet having a head and a foot, the head and the foot covering different areas.

11. The plate of claim 9, wherein the marker comprises:
a front frame; and
a back frame;
the front frame and the back frame covering different areas.

12. The plate of claim 9, wherein the marker comprises:
a front-side pattern always present in the image; and
a back-side pattern present in the image in combination with the front-side pattern after exposure from the back side.

13. The plate of claim 9, wherein the marker comprises:
a corner element having a front and a back, the front and the back covering different areas not including a region of interest.

14. The plate of claim 9, having a layer sensitive to the radiation that is readable only from the front side, the back side marker further comprising at least one of a material that enhances reading the sensitive layer and a material that attenuates reading of the sensitive layer.

15. The plate of claim 9, wherein the back side marker further comprises at least one of a material that enhances exposure of the plate in a defined region and a material that attenuates exposure of the plate in the defined region.

16. The plate of claim 15, wherein the back side marker further comprises one of a heavy element, an alloy including a heavy element, a compound including a heavy element or a salt of a heavy element.

17. The plate of claim 16, the heavy element being one of Pb, Sn, Bi, I and Ba.

18. The plate of claim 1, further comprising a front side marker producing a mark in the image whose appearance in the image on the plate indicates exposure from the front side.

19. The plate of claim 18, having a layer sensitive to the radiation that is readable at least from the front side, the front side marker further comprising at least one of a void defined in the layer sensitive to the radiation, a material that enhances a signal returned in the area of the marker when reading the sensitive layer and a material that attenuates the signal returned in the area of the marker when reading the sensitive layer.

20. The plate of claim 19, readable only from the front side by exciting the layer sensitive to the radiation with an excitation wavelength to generate a return signal at a return signal wavelength, the front side marker functionally opaque to at least one of the excitation signal wavelength and the return signal wavelength.

21. The plate of claim 19, wherein the front side marker further comprises one of a heavy element, an alloy including a heavy element, a compound including a heavy element or a salt of a heavy element.

22. The plate of claim 21, the heavy element being one of Pb, Sn, Bi, I and Ba.

23. The plate of claim 19, wherein the front side marker further comprises a void defined in the layer sensitive to the radiation.

24. The plate of claim 1, the marker having asymmetry about at least one axis and the marker further comprising a front side marker and a back side marker.

25. The plate of claim 24, wherein the marker has horizontal asymmetry about a vertical axis relative to a normal image orientation.

26. The plate of claim 25, wherein the front side marker further comprises:
a region defined to have a directional marker shape pointed in a first direction when viewed from the front side.

27. The plate of claim 26, wherein the back side marker further comprises:
a region defined to have a directional marker shape pointed in a second direction different from the first direction when viewed from the front side.

28. The plate of claim 27, wherein the back side marker is positioned so as to alter the appearance in the image of the front side marker when the plate is exposed from the back side and read from the front side.

29. The plate of claim 24, wherein the marker has vertical asymmetry about a vertical axis relative to a normal image orientation.

30. The plate of claim 29, wherein the front side marker further comprises:
a region defined to have a directional marker shape pointed in a first direction when viewed from the front side.

31. The plate of claim 30, wherein the back side marker further comprises:
a region defined to have a directional marker shape pointed in a second direction different from the first direction when viewed from the front side.

32. The plate of claim 31, wherein the back side marker is positioned so as to obscure the front side marker when the plate is exposed from the back side and read from the front side.

33. The plate of claim 19, further comprising another sensitive layer, wherein the back side marker is disposed between the sensitive layer and the other sensitive layer, and the plate further comprising another front side marker relative to the other sensitive layer.

34. The plate of claim 1, configured for use as radiography plate having a substantially smooth surface capable of producing a diagnostically useful image when exposed from either one of two sides.

35. The plate of claim 34, wherein the feature comprises:
a front side marker producing a mark always apparent in the image; and
a back side marker producing a mark apparent in the image when the plate is exposed from the back side.

36. The plate of claim 35, wherein the mark produced by the back side marker at least partially overlaps the front side mark.

37. The plate of claim 36, wherein the mark produced by the front side marker and the mark produced by the back side marker are each asymmetric about two substantially perpendicular axes.

38. The plate of claim 37, included in a radiography system further comprising:
software defined by a computer executed sequence of instructions to:
store the image in an image file containing image data;
detect the mark in the image data;
arrange the image data for display in a selected arrangement relative to a diagnostically expected orientation; and
store with the image file, distinct from the image data, an indication of the selected arrangement of the image data.

39. A method of identifying a side from which a radiation-recording plate having a capacity to form an image of an object upon exposure to radiation impinging on the object and then incident upon the plate from a front side and having a capacity to form an image of an object upon exposure to radiation impinging on the object and then incident upon the plate from a back side has been exposed to radiation, comprising:
exposing the plate to the radiation incident upon the plate from only one of the front side and the back side without constraint as to which;
obtaining an image of the object produced by exposing the plate to the radiation impinging on the object and then incident upon the plate; and
incorporating in the plate prior to exposure, in a position that substantially does not interfere with an image area of the plate, a marker producing a mark whose appearance in an image identifies both which side the plate is exposed from and which is indicative of any mirroring transformations performed upon an image recovered from the plate after exposure; and
observing the image for the identification of the side of the plate exposed and for the indication of any mirroring transformations.

40. The method of claim 39, further comprising:
arranging the marker to produce the mark so as to indicate whether the plate was flipped or rotated prior to exposing; and
observing the image for the indication.

41. The method of claim 40, further comprising:
observing the image using image processing software, the image processing software recognizing the mark and reorienting the image to have a clinically expected orientation.

42. The method of claim 41, further comprising:
storing with the image an indication of whether the image has been flipped an odd number of times.

43. The method of claim 41, further comprising:
substituting for the mark a replacement mark indicative of the software having processed the image;
storing the image with the replacement mark.

44. The method of claim 43, wherein substituting further comprises:
arranging the replacement mark to be visible and asymmetric with respect to both axes whereby the replacement mark indicates an orientation of the image that is recognizable with respect to both axes.

45. The method of claim 43, further comprising:
storing with the image an indication of whether the image has been reoriented by an odd number of times.

46. A method of making a radiation sensitive plate having at least one radiation sensitive layer, comprising:
providing a film sensitive to the radiation on a first side of the radiation sensitive plate;
applying a suspension of a heavy metal in a binder to a region of a second side of the radiation sensitive layer;
providing a detectable marker on the first side; and
wherein
the detectable marker and the suspension of a heavy metal applied combined are distinct and asymmetric.

47. An image storage device holding an image data structure comprising:
a recording medium;
a data structure defined by a record in the recording medium of an image produced by exposure to radiation of a radiation-sensitive medium; and
a mark embedded in the data structure, the mark produced during the exposure of the radiation-sensitive medium, and the mark both indicative of which side the radiation-sensitive medium was exposed from and indicative of any mirroring transformations performed upon the image in whose record the mark is embedded.

48. The image storage device of claim 47, wherein the mark further comprises:
an indication of laterality immune to confusion by flipping and rotating the image.

49. The image storage device of claim 48, wherein the recording medium is the radiation-sensitive medium.

50. The image storage device of claim 48, wherein the record in the recording medium comprises:
a digital signal representing the image held by the recording medium.

51. The image storage device of claim 50, further comprising:
a record of current orientation of the image, independent of the digital signal representing the image.

52. The image storage device of claim 48, wherein the indication of laterality further comprises:
a record apparent upon viewing the image identifying unambiguously a current orientation of the image.

* * * * *